United States Patent
Libbus et al.

(10) Patent No.: US 7,894,895 B2
(45) Date of Patent: *Feb. 22, 2011

(54) SYSTEM AND METHOD FOR TESTING NEURAL STIMULATION THRESHOLD

(75) Inventors: Imad Libbus, St. Paul, MN (US); Andrew P. Kramer, Marine on St. Croix, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,370

(22) Filed: Aug. 23, 2010

(65) Prior Publication Data

US 2010/0318154 A1    Dec. 16, 2010

Related U.S. Application Data

(63) Continuation of application No. 11/279,188, filed on Apr. 10, 2006, now Pat. No. 7,783,349.

(51) Int. Cl.
  *A61N 1/00*    (2006.01)
(52) U.S. Cl. .......................................................... 607/4
(58) Field of Classification Search ...................... 607/4, 607/9, 62; 600/17, 509, 510
  See application file for complete search history.

(56) References Cited

U.S. PATENT DOCUMENTS

| | | | |
|---|---|---|---|
| 5,603,331 A | 2/1997 | Heemels et al. | |
| 6,026,320 A | 2/2000 | Carlson et al. | |
| 6,301,499 B1 | 10/2001 | Carlson et al. | |
| 6,529,772 B2 | 3/2003 | Carlson et al. | |
| 6,678,547 B2 | 1/2004 | Carlson et al. | |
| 6,718,197 B1 | 4/2004 | Carlson et al. | |
| 6,748,272 B2 | 6/2004 | Carlson et al. | |
| 7,062,314 B2 | 6/2006 | Zhu et al. | |
| 7,079,887 B2 | 7/2006 | Burnes et al. | |
| 2003/0040774 A1 | 2/2003 | Terry et al. | |
| 2003/0199937 A1 | 10/2003 | Carlson | |
| 2004/0158295 A1 | 8/2004 | Dyjach et al. | |
| 2004/0186525 A1* | 9/2004 | Burnes et al. | 607/17 |
| 2004/0193066 A1 | 9/2004 | Carlson et al. | |
| 2004/0210261 A1 | 10/2004 | King et al. | |
| 2004/0230241 A1 | 11/2004 | Carlson et al. | |

(Continued)

OTHER PUBLICATIONS

Adamopoulos, S., "Effects of pulsed beta-stimulant therapy on beta-adrenoceptors and chronotropic responsiveness in chronic heart failure.", Lancet, 345(8946), (Feb. 11, 1995), 344-9.

(Continued)

*Primary Examiner*—Niketa I Patel
*Assistant Examiner*—Robert N Wieland
(74) *Attorney, Agent, or Firm*—Schwegman, Lundberg & Woessner, P.A.

(57) ABSTRACT

Various system embodiments comprise a neural stimulator, a premature ventricular contraction (PVC) event detector, a heart rate detector, an analyzer, and a controller. The neural stimulator is adapted to generate a stimulation signal adapted to stimulate an autonomic neural target. The analyzer is adapted to, in response to a PVC event signal from the PVC event detector, generate an autonomic balance indicator (ABI) as a function of pre-PVC heart rate data and post-PVC heart rate data. Other aspects and embodiments are provided herein.

28 Claims, 13 Drawing Sheets

U.S. PATENT DOCUMENTS

| | | |
|---|---|---|
| 2005/0090719 A1 | 4/2005 | Scheiner et al. |
| 2005/0149132 A1 | 7/2005 | Libbus |
| 2005/0234353 A1 | 10/2005 | Xue et al. |
| 2005/0261741 A1 | 11/2005 | Libbus et al. |
| 2006/0106428 A1 | 5/2006 | Libbus et al. |
| 2006/0106429 A1 | 5/2006 | Libbus et al. |
| 2006/0135998 A1 | 6/2006 | Libbus et al. |
| 2007/0276453 A1 | 11/2007 | Hill et al. |
| 2008/0086182 A1 | 4/2008 | Ben-David et al. |

OTHER PUBLICATIONS

Bauer, A., et al., "Turbulence dynamics: an independent predictor of late mortality after acute myocardial infarction.", Int J Cardiol., 107(1), (2006), 42-7.

Coats, A. J., "Controlled trial of physical training in chronic heart failure. Exercise performance, hemodynamics, ventilation, and autonomic function.", Circulation, 85(6), (Jun. 1992), 2119-31.

Iwasa, A., et al., "Abnormal heart rate turbulence predicts the initiation of ventricular arrhythmias.", Pacing Clin Electrophysiol., 28(11), (2005), 1189-97.

Leier, C. V., "Drug-induced conditioning in congestive heart failure.", Circulation, 65(7), (Jun. 1982), 1382-7.

Liang, C., "Conditioning effects of chronic infusions of dobutamine. Comparison with exercise training.", Journal of Clinical Investigation, 64(2), (Aug. 1979), 613-9.

Malberg, H., et al., "Short-term Heart Rate Turbulence Analysis Versus Variability and Baroreceptor Sensitivity in Patients With Dilated Cardiomyopathy.", Indian Pacing Electrophysiol J., 4(4), (2004), 162-75.

Moore, R. K., et al., "Heart rate turbulence and death due to cardiac decompensation in patients with chronic heart failure.", Eur J Heart Fail., 8(6), (2006), 585-90.

Schwab, J. O., et al., "Influence of basic heart rate and sex on heart rate turbulence in healthy subjects.", Pacing Clin Electrophysiol., 27(12), (2004), 1625-1631.

Wichterle, D., et al., "Hemodynamics and autonomic control of heart rate turbulence.", J Cardiovasc Electrophysiol., 17(3), (2006), 286-91.

Wichterle, D., et al., "Turbulence slope after atrial premature complexes is an independent predictor of mortality in survivors of acute myocardial infarction.", J Cardiovasc Electrophysiol., 15(12), (2004), 1350-6.

* cited by examiner ies, for example.

SYSTEM AND METHOD FOR TESTING NEURAL STIMULATION THRESHOLD

CLAIM OF PRIORITY

This application is a continuation of and claims the benefit of priority under 35 U.S.C. §120 to U.S. patent application Ser. No. 11/279,188, filed on Apr. 10, 2006, now issued as U.S. Pat. No. 7,783,349, which is hereby incorporated by reference herein in its entirety.

CROSS REFERENCE TO RELATED APPLICATIONS

The following commonly assigned U.S. patent applications are related, and are herein incorporated by reference in their entirety: "Automatic Baroreflex Modulation Based on Cardiac Activity," Ser. No. 10/746,846, filed on Dec. 24, 2003, now abandoned; "System and Method For Closed-Loop Neural Stimulation," Ser. No. 11/280,940, filed on Nov. 16, 2005; "System and Method For Closed-Loop Neural Stimulation," Ser. No. 10/992,319, filed on Nov. 18, 2004; and "Cardiac Rhythm Management Device With Neural Sensor," Ser. No. 10/992,320, filed on Nov. 18, 2004, now U.S. Pat. No. 7,769,450.

TECHNICAL FIELD

This application relates generally to neural stimulation systems and, more particularly, to systems, devices and methods for providing closed-loop neural stimulation.

BACKGROUND

The automatic nervous system (ANS) regulates "involuntary" organs and maintains normal internal function and works with the somatic nervous system. The ANS includes the sympathetic nervous system and the parasympathetic nervous system. The sympathetic nervous system is affiliated with stress and the "fight or flight response" to emergencies, and the parasympathetic nervous system is affiliated with relaxation and the "rest and digest response." Autonomic balance reflects the relationship between parasympathetic and sympathetic activity. Changes in autonomic balance are reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

It is desirable to use a measurement of autonomic balance in order to appropriately control or titrate various neural stimulation therapies. Neural stimulators have been proposed to treat a variety of disorders, such as epilepsy, obesity, breathing disorders, hypertension, post myocardial infarction (MI) remodeling and heart failure. Direct electrical stimulation has been applied to the carotid sinus and vagus nerve. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Electrical systems have been proposed to treat hypertension in patients who do not otherwise respond to therapy involving lifestyle changes and hypertension drugs, and possibly to reduce drug dependency for other patients. The stimulation of sympathetic afferents triggers sympathetic activation, parasympathetic inhibition, vasoconstriction, and tachycardia. In contrast, parasympathetic activation results in bradycardia, vasodilation and inhibition of vasopressin release. Direct stimulation of the vagal parasympathetic fibers has been shown to reduce heart rate. In addition, some research indicates that chronic stimulation of the vagus nerve may be of protective myocardial benefit following cardiac ischemic insult. Reduced autonomic balance (increase in sympathetic and decrease in parasympathetic cardiac tone) during heart failure has been shown to be associated with left ventricular dysfunction and increased mortality. Research also indicates that increasing parasympathetic tone and reducing sympathetic tone may protect the myocardium from further remodeling and predisposition to fatal arrhythmias following myocardial infarction.

SUMMARY

Various aspects of the present subject matter relate to a system. Various system embodiments comprise a neural stimulator, a premature ventricular contraction (PVC) event detector, a heart rate detector, an analyzer, and a controller. The neural stimulator is adapted to generate a stimulation signal adapted to stimulate an autonomic neural target. The analyzer is adapted to, in response to a PVC event signal from the PVC event detector, generate an autonomic balance indicator (ABI) as a function of pre-PVC heart rate data and post-PVC heart rate data.

Various aspects of the present subject matter relate to a method. According to various embodiments of the method, an autonomic neural target is stimulated, a PVC event is identified, and pre-PVC heart rate data and post-PVC heart rate data are detected. An autonomic balance indicator (ABI) is generated as a function of the pre-PVC heart rate data and the post-PVC heart rate data in response to the PVC event.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
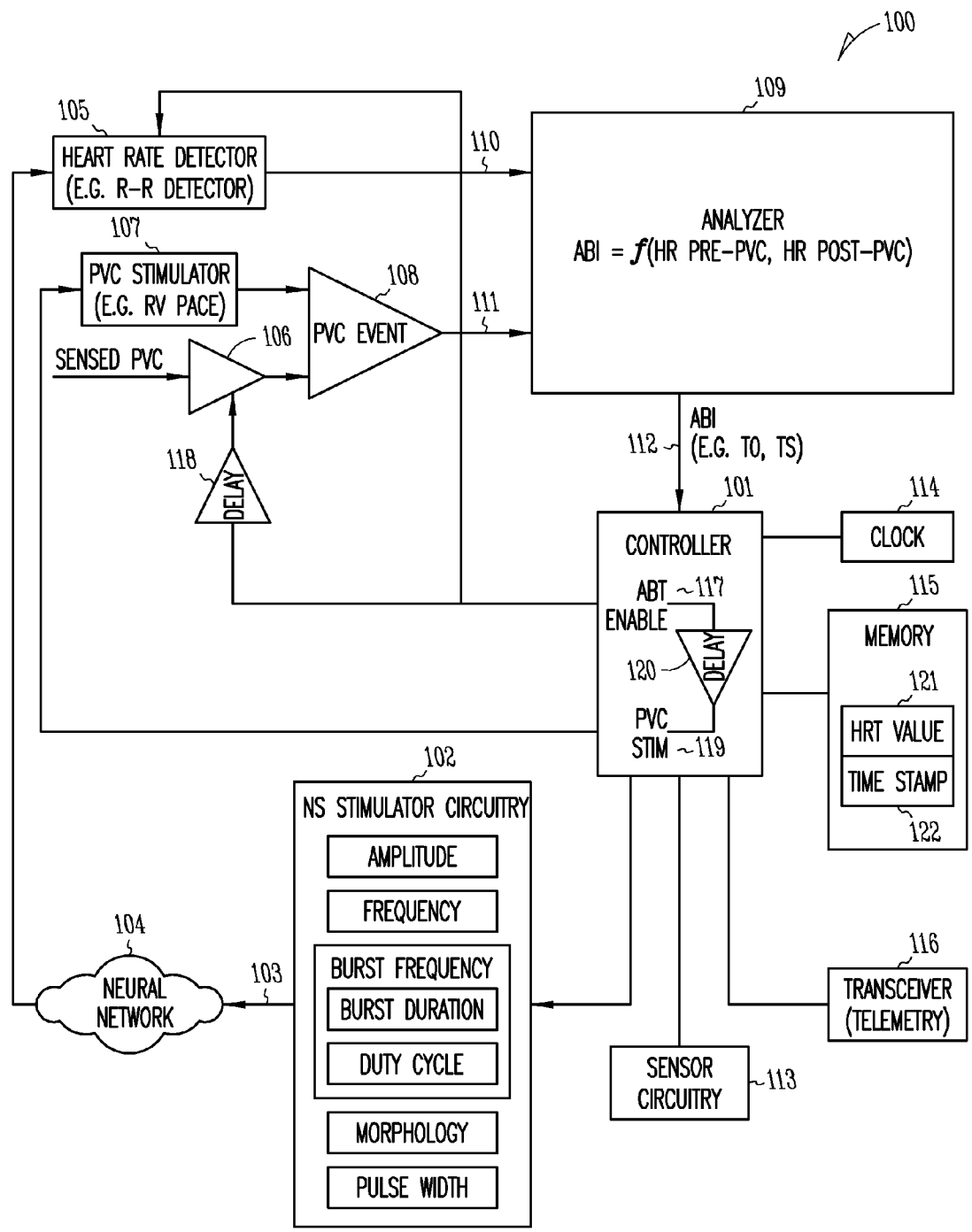
FIG. 1 illustrates a neural stimulator with autonomic balance feedback, according to various embodiments of the present subject matter.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various aspects of the present subject matter monitor autonomic balance for use in titrating a neural stimulation therapy. Various aspects of the present subject matter monitor autonomic balance for use in determining whether neural stimulation is capturing the appropriate neural networks. A value for the autonomic balance is determined at discrete times corresponding to premature ventricular contractions (PVC). The autonomic balance value is based on the heart rate before the PVC and the heart rate after the PVC. The PVC can be a detected, naturally-occurring PVC or an induced PVC. The autonomic balance values can be trended over a period of time to determine the efficacy of the neural therapy. Benefits include the ability to quickly determine, in near real time, a value for autonomic balance. The autonomic balance value can be found at discrete times with relatively small requirements for power and for data processing and storage.

Provided below is a brief discussion of the autonomic nervous system, and methods for assessing autonomic balance, including a brief comparison of Heart Rate Turbulence (HRT) to Heart Rate Variability (HRV). Neural stimulation therapy examples, with and without myocardial stimulation therapy, are discussed. This disclosure concludes with examples of implantable medical devices and methods, and examples of implantable medical device systems.

Autonomic Nervous System

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Stimulating the sympathetic and parasympathetic nervous systems can have a number of physiological effects. For example, stimulating various portions of the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating various portions of the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Autonomic Balance Assessment

Heart Rate Variability (HRV) is one technique that has been proposed to assess autonomic balance. The time interval between intrinsic ventricular heart contractions changes in response to the body=s metabolic need for a change in heart rate and the amount of blood pumped through the circulatory system. For example, during a period of exercise or other activity, a person=s intrinsic heart rate will generally increase over a time period of several or many heartbeats. However, even on a beat-to-beat basis, that is, from one heart beat to the next, and without exercise, the time interval between intrinsic heart contractions varies in a normal person. These beat-to-beat variations in intrinsic heart rate are the result of proper regulation by the autonomic nervous system of blood pressure and cardiac output; the absence of such variations indicates a possible deficiency in the regulation being provided by the autonomic nervous system. One method for analyzing HRV involves detecting intrinsic ventricular contractions, and recording the time intervals between these contractions, referred to as the R-R intervals, after filtering out any ectopic contractions (ventricular contractions that are not the result of a normal sinus rhythm). This signal of R-R intervals is typically transformed into the frequency-domain, such as by using fast Fourier transform (AFFT ⓔ) techniques, so that its spectral frequency components can be analyzed and divided into low and high frequency bands. For example, the low frequency (LF) band can correspond to a frequency (Af ⓔ) range 0.04 Hz #f<0.15 Hz, and the high frequency (HF) band can correspond to a frequency range 0.15 Hz #f#0.40 Hz. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health. A spectral analysis of the frequency components of the R-R interval signal can be performed using a FFT (or other parametric transformation, such as autoregression) technique from the time domain into the frequency domain. Such calculations require significant amounts of data storage and processing capabilities. Additionally, such transformation calculations increase power consumption, and shorten the time during which the implanted battery-powered device can be used before its replacement is required.

The present subject matter provides a neural stimulator that monitors autonomic feedback. The neural stimulator provides a value for autonomic balance at discrete times corresponding to premature ventricular contractions (PVC) based on the heart rate for a predetermined number of beats before the PVC and the heart rate for a predetermined number of beats after the PVC.

Heart rate turbulence (HRT) is the physiological response of the sinus node to a PVC, consisting of a short initial heart rate acceleration followed by a heart rate deceleration. HRT has been shown to be an index of autonomic function, closely correlated to HRV. HRT is believed to be an autonomic baroreflex. The PVC causes a brief disturbance of the arterial blood pressure (low amplitude of the premature beat, high amplitude of the ensuing normal beat). This fleeting change is registered immediately with an instantaneous response in the form of HRT if the autonomic system is healthy, but is either weakened or missing if the autonomic system is impaired.

By way of example and not limitation, it has been proposed to quantify HRT using Turbulence Onset (TO) and Turbulence Slope (TS). TO refers to the difference between the heart rate immediately before and after a PVC, and can be expressed as a percentage. For example, if two beats are evaluated before and after the PVC, TO can be expressed as:

$$TO\% = \frac{(RR_{+1} + RR_{+2}) - (RR_{-2} - RR_{-1})}{(RR_{-2} - RR_{-1})} * 100.$$

$RR_{-2}$ and $RR_{-1}$ are the first two normal intervals preceding the PVC and $RR_{+1}$ and $RR_{+2}$ are the first two normal intervals following the PVC. In various embodiments, TO is determined for each individual PVC, and then the average value of all individual measurements is determined. However, TO does not have to be averaged over many measurements, but can be based on one PVC event. Positive TO values indicate deceleration of the sinus rhythm, and negative values indicate acceleration of the sinus rhythm. The number of R-R intervals analyzed before and after the PVC can be adjusted according to a desired application. TS, for example, can be calculated as the steepest slope of linear regression for each sequence of five R-R intervals. In various embodiments, the TS calculations are based on the averaged tachogram and expressed in milliseconds per RR interval. However, TS can be determined without averaging. The number of R-R intervals in a sequence used to determine a linear regression in the TS calculation also can be adjusted according to a desired application.

In its use of HRT, the present subject matter provides rules or criteria for use to select PVCs and for use in selecting valid R-R intervals before and after the PVCs. A PVC event can be defined by an R-R interval in some interval range that is shorter than a previous interval by some time or percentage, or it can be defined by an R-R interval without an intervening P-wave (atrial event) if the atrial events are measured. Various embodiments select PVCs only if the contraction occurs at a certain range from the preceding contraction and if the contraction occurs within a certain range from a subsequent contraction. For example, various embodiments limit the HRT calculations to PVCs with a minimum prematurity of 20% and a post-extrasystole interval which is at least 20% longer than the normal interval. Additionally, pre-PVC R-R and post-PVC R-R intervals are considered to be valid if they satisfy the condition that none of the beats are PVCs. One HRT process, for example, excludes R-R intervals that are less than a first time duration, that are longer than a second time duration, that differ from a preceding interval by more than a third time duration, or that differ from a reference interval by a predetermined amount time duration or percentage. In an embodiment of such an HRT process with specific values, R-R intervals are excluded if they are less than 300 ms, are more than 2000 ms, differ from a preceding interval by more than 200 ms, or differ by more than 20% from the mean of the last five sinus intervals. Various embodiments of the present subject matter provide programmable parameters, such as any of the parameters identified above, for use in selecting PVCs and for use in selecting valid R-R intervals before and after the PVCs.

The neural stimulation device that incorporates this technique for assessing autonomic balance can be used to provide either parasympathetic stimulation or inhibition or sympathetic stimulation or inhibition. Various device embodiments include means for pacing a ventricle, such as at least one ventricular pacing lead. To measure autonomic balance for closed-loop therapy titration, the device intermittently introduces or senses a PVC, and measures the resulting heart rate turbulence, as described above. In this way the therapy intensity can be increased or decreased according to the patient's autonomic balance. Various embodiments introduce a PVC and monitor autonomic balance to verify that a neural stimulation therapy is capturing the desired neural network. Various device embodiments perform an auto-threshold detection, in which the device automatically adjusts neural stimulation parameters and/or neural stimulation target locations until the desired autonomic balance reaction is observed. Other embodiments report out a value for the autonomic balance for use in programming the neural stimulation.

Benefits of using HRT to monitor autonomic balance include the ability to measure autonomic balance at a single moment in time. Additionally, unlike the measurement of HRV, HRT assessment can be performed in patients with frequent atrial pacing. Further, HRT analysis provides for a simple, non-processor-intensive measurement of autonomic balance. Thus, data processing, data storage, and data flow are relatively small, resulting in a device with less cost and less power consumption. Also, HRT assessment is faster than HRV, requiring much less R-R data. HRT allows assessment over short recording periods similar in duration to typical neural stimulation burst durations, such as on the order of tens of seconds, for example.

Various implantable device embodiments provide autonomic stimulation therapy. The device periodically or intermittently introduces PVC and measures HRT for closed-loop therapy titration and/or for auto-threshold determination. The present subject matter can be used in any patient population which may benefit from autonomic neural stimulation therapy, including patients with heart failure, coronary artery disease, dysautonomia, and the like. However, the present subject matter is not suitable for patients dependent on atrial pacing, because heart rate will be controlled by the pacemaker rather than the cardiac autonomic control system. In various embodiments, the present subject matter is implemented in an implantable cardiac rhythm management (CRM) device, such as a pacemaker, an anti-tachycardia device such as a defibrillator or cardioverter, CRT-pacing device, or CRT defibrillation/cardioversion device. According to various embodiments, the device detects the presence of a PVC and calculates the resulting HRT. In some embodiments, the device artificially introduces a PVC and calculates the resulting HRT. In some embodiments, the device receives a message indicating a PVC event has or will be occurring.

The following section discusses neural stimulation therapies, and provides some information regarding pacing/cardioverting therapies, and CRT. These CRM functions can be used to detect a PVC or induce a PVC. There are other benefits of integrating a neural stimulator with a CRM device.

Therapy Examples

Embodiments of the present subject matter use autonomic balance as a feedback for neural stimulation, and embodiments of the present subject matter determine neural stimulation thresholds using an autonomic balance indicator as a surrogate of capture.

NS: ABI To Titrate Neural Stimulation

According to an embodiment, an autonomic balance indicator (ABI) provides feedback to titrate a neural stimulation therapy to achieve a desired autonomic balance. Various embodiments average or trend discrete autonomic balance measurements, and use the trended value as feedback for the neural stimulation control system. Thus, the present subject matter does not overcompensate with a neural stimulation adjustment in response to one or a few autonomic indicators. Embodiments of the present subject matter provide neural stimulation to an autonomic nerve to adjust the autonomic balance, and some embodiments stimulate an autonomic nerve (e.g. vagus) as part of various therapies such as therapies to treat obesity, epilepsy, breathing disorders, and hypertension.

According to a closed-loop system embodiment, the device is used to evaluate chronic autonomic balance condition concomitant with long-term neural stimulation therapy, and to adjust the neural stimulation level to achieve a desired autonomic balance. According to some embodiments, the ABI may be determined during periods without neural stimulation or the neural stimulation therapy may be interrupted to obtain an ABI measure in order to measure a steady-state patient condition rather than a transient response to neural stimulation. Some embodiments determine ABI at the beginning of neural stimulation, during neural stimulation, or at the end of neural stimulation.

According to various embodiments, the present subject matter provides neural stimulation to stimulate or inhibit the sympathetic system or to stimulate or inhibit the parasympathetic system. Some embodiments increase the amount of sympathetic nerve traffic to the myocardium to treat conditions in which an increase in heart rate or an increase in the inotropic state of the heart is desirable. Examples of such situations include bradycardia and acute cardiac failure.

Some embodiments of the present subject matter pace the heart to treat arrhythmias by stimulating the autonomic nerves rather than stimulating the myocardium. The heart can be paced using the autonomic nervous system to provide chronotropic and inotropic control via selective cardiac neural stimulation. The selective neural stimulation provide a natural stimulus for pacing.

Selective stimulation of epicardial autonomic ganglia can be used to selectively activate the parasympathetic nervous system. Embodiments of the present subject matter decrease left ventricular contractility via postganglionic parasympathetic nervous system activity. The intrinsic cardiac ganglionated plexus integrate and process afferent and efferent autonomic nervous system activity. Some embodiments provide selective neural stimulation to provide specific cardiac pacing effects based on the stimulated fat pad.

Embodiments of the present subject matter stimulate neural pathways to fine-tune autonomic balance to mitigate a number of cardiovascular disorders. Ischemia, which may occur because of coronary artery disease, can cause increased sympathetic nervous system activity. This increased sympathetic activity can result in increased exposure of the myocardium to epinephrine and norepinephrine. These catecholamines activate intracellular pathways within the myocytes, which lead to myocardial death and fibrosis. Stimulation of the parasympathetic nerves inhibits the effect from the ischemia-induced increase in sympathetic activity. Some embodiments provide selective neural stimulation to increase vagal tone to reduce myocardial exposure to epinephrine, thus reducing myocardial death and fibrosis. Some embodiments provide selective neural stimulation to increase vagal tone to prevent post-MI patients from further remodeling or predisposition to fatal arrhythmias. Some embodiments provide selective neural stimulation to provide autonomic balance following ischemic insult to prevent the onset of lethal arrhythmias.

NS: ABI To Verify Neural Stimulation Capture

According to an embodiment, a neural stimulation threshold or auto-threshold system determines, using an ABI measurement, whether a given neural stimulation evokes a response above some threshold. Thus, a certain ABI response is used to determine that a particular neural stimulation is capturing the appropriate neural networks. For example, the threshold testing can apply demanded testing, such as testing triggered by a physician command or an intermittent measurement based on time. The testing could also be triggered by an event. A system embodiment with demanded testing is able to stimulate PVCs on demand. A method embodiment includes triggering or requesting a threshold test, turning on the neural stimulation at a given level, recording the pre-PVC R-R intervals, stimulating a PVC, recording the post-PVC R-R intervals, and calculating the ABI during the neural stimulation using the pre-PVC and post-PVC R-R intervals.

The ABI measurement can be reported to a programmer, where a physician can manually take some action or the programmer can automatically step the neural stimulation to the next level and trigger another test. The ABI can be used by the neural stimulator device to automatically step the neural stimulation and trigger another test. For example, the device can be programmed to look for a "threshold" stimulation based on a specified ABI response and perform the auto-threshold test and adjust neural stimulation until the "threshold" is achieved, with some limits on the range of neural stimulation levels. The device can store ABI values in memory or use the ABI result to adjust the neural stimulation level.

Various embodiments verify stimulation capture at or near the time of implantation of a neural stimulator. A temporary pacing catheter can be implanted, if an existing CRM lead is not already available, for use to generate PVCs and whether the implanted stimulator is adequately capturing the neural stimulation. These induced PVCs can be used to determine neural stimulation threshold and verify capture for the implanted neural stimulator. Thus, such a system is useful to determine good placement of a neural stimulator, such as placement of a neural stimulator lead. Some embodiments use the system to select an appropriate electrical vector between or among available neural stimulation electrodes. Some embodiments use ABI measurement(s) to otherwise focus the neural stimulation, such as focused ultrasound stimulation, to provide selective neural stimulation.

According to various embodiments, the neural stimulation with an autonomic balance indicator is included in a system that has myocardial stimulation capabilities. The system can include at least one device with both CRM and neural stimulation functions in each device, and can include a CRM device and a neural stimulation device adapted to communicate with each other.

CRM: Pacing/Cardioverting (Defibrillating, Anti-Tachycardia Pacing)

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses a CRM system. Such systems are often implanted in the patient and deliver therapy to the heart.

CRM systems include, among other things, pacemakers. Pacemakers deliver timed sequences of low energy electrical stimuli, called pace pulses, to the heart. Intravascular lead-wire or catheter (referred to as a "lead") having one or more electrodes disposed in or about the heart can be used to deliver the stimulation. Some embodiments use a "planet" IMD wirelessly connected to "satellite" electrodes to deliver the stimulation. Heart contractions are initiated in response to such pace pulses. By properly timing the delivery of pace pulses, the heart can be induced to contract in proper rhythm, greatly improving its efficiency as a pump. Pacemakers are often used to treat patients with bradyarrhythmias, that is, hearts that beat too slowly, or irregularly.

A variety of cardiac pacemakers are known and commercially available. Pacemakers are generally characterized by a number of different aspects of their construction or use, such as which chambers of the heart they are capable of sensing, the chambers to which they deliver pacing stimuli, and their responses, if any, to sensed intrinsic electrical cardiac activity.

Some pacemakers deliver pacing stimuli at fixed, regular intervals without regard to naturally occurring cardiac activity. Some pacemakers sense electrical cardiac activity in one or more of the chambers of the heart, and inhibit or trigger delivery of pacing stimuli to the heart based on the occurrence and recognition of sensed intrinsic electrical events. One such pacemaker, for example, senses electrical cardiac activity in the ventricle of the patient's heart, and delivers pacing stimuli to the ventricle only in the absence of electrical signals indicative of natural ventricular contractions. Another type of pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by the second type of pacemaker is timed using prior sensed or paced events.

Pacemakers are also known which respond to other types of physiologically-based signals, such as signals from sensors for measuring the pressure inside the patient's ventricle or for measuring the level of the patient's physical activity. In some rate-responsive pacemakers, the pacing rate is determined according to the output from an activity sensor. The pacing rate is variable between a predetermined maximum and minimum level, which may be selectable from among a plurality of programmable upper and lower rate limit settings. When the activity sensor output indicates that the patient's activity level has increased, the pacing rate is increased from the programmed lower rate by an incremental amount which is determined as a function of the output of the activity sensor.

CRM systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart is not allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. Some CRM systems also are pacemakers/defibrillators that combine the functions of pacemakers and defibrillators, drug delivery devices, and any other implantable or external systems or devices for diagnosing or treating cardiac arrhythmias. A cardioverter embodiment treats arrhythmias using anti-tachycardia pacing.

CRM: Cardiac Resynchronization Therapy (CRT)

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) accounts for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed CRT. Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

Clinical data has shown that CRT, achieved through synchronized biventricular pacing, results in a significant improvement in cardiac function. It has also been reported that CRT can be beneficial in preventing and/or reversing the ventricular remodeling that often occurs in post-MI and heart failure patients. Remodeling control therapy (RCT) can be provided by controlling ventricular activation with cardiac resynchronization pacing of the myocardium.

Neural stimulation can also be applied as part of CRT. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction. Thus, some embodiments that provide CRT includes anti-remodeling therapy (ART) by stimulating the baroreflex in order to inhibit sympathetic activity to provide a greater therapeutic benefit than either RCT or ART individually. Additional information regarding the use of neural stimulation for anti-remodeling therapy (ART) is provided in U.S. Pat. No. 7,260,431 entitled "Combined Remodeling Control Therapy and Anti-Remodeling Therapy By Implantable Cardiac Device", filed May 20, 2004, which is herein incorporated by reference in its entirety.

An implantable stimulating electrode is placed near autonomic nerves. Some embodiments use epicardial leads for epicardial stimulation of a target neural stimulation site, some embodiments use intravascular leads for transvascular neural stimulation of a target neural stimulation site, and some embodiments use intravascular leads adapted to puncture a vessel for percutaneous stimulation of a target neural stimulation site, and some embodiments use a neural stimulation cuff electrode. The nerves can be stimulated using electrical stimulation pulses, or can be stimulated using other energy sources such as sound (e.g. ultrasound) or light stimulation. An implantable pulse generator with programmable pulse generating features is attached to the electrode. Electrical activation of the electrode(s) stimulates the target sympathetic or parasympathetic nerves anatomically located near the electrode(s) at a strength and frequency sufficient to elicit depolarization of the adjacent nerve(s).

Electrical neural stimulation may be applied near the myocardium. Some embodiments electrically stimulate autonomic nerves innervating the myocardium without eliciting depolarization and contraction of the myocardium directly because the threshold for neural depolarization (especially myelinated vagal nerve fibers of the parasympathetic nervous system) is much lower than that of myocardial tissue. Differing frequencies of stimulation can be used so as to depolarize post (or pre in case of vagal nerve stimulation) ganglionic nerve fibers. A stimulus response curve may be generated to determine the minimal threshold required to elicit myocardial contraction, and still maintain neural depolarization of the site. Some embodiments time the neural stimulation with the refractory period.

Some embodiments stimulate fat pads. Some embodiments stimulate an SVC-AO cardiac fat pad located proximate to a junction between a superior vena cava and an aorta. Stimulation of the SVC-AO fat pad specifically reduces the contractility of the left ventricle, thus providing a neural stimulation treatment for diseases such as heart failure and/or post myocardial infarction remodeling. Some embodiments stimulate a PV cardiac fat pad associated with an sinoatrial (SA) node and some embodiments stimulate an IVC-LA cardiac fat pad associated with an atrioventricular (AV) node. The PV cardiac fat pad is located proximate to a junction between a right atrium and right pulmonary vein, and the IVC-LA cardiac fat pad is located proximate to a junction between an inferior vena cava and a left atrium. Stimulation of the PV cardiac fat pad reduces a sinus rate, and stimulation of the IVC-LA fat pad increases AV conduction, which affects timing between a contractions in a right atrium and contractions in the right ventricle. Fat pad stimulation activates parasympathetic efferents. Because fat pad ganglia form part of the efferent pathway, stimulation of cardiac fat pads directly effects cardiac tissue. For example, stimulating the parasympathetic efferents can selectively affect rate, and conduction. Stimulation of the parasympathetic also has post-ganglionic inhibition of sympathetic outflow.

Satellite electrodes or leads can be used to deliver the selective neural stimulation to a cardiac neural stimulation site, and other non-electrical neural stimulators can be used. Examples of non-electrical neural stimulators include stimulators that use ultrasound and light energies, for example. Lead embodiments include epicardial leads and intravascularly-fed leads. Various lead embodiments are designed and positioned to provide multiple functions such as sensing, pacing, anti-tachycardia therapy etc. in addition to neural stimulation. Various embodiments use an epicardial, transvascular and/or percutaneous approaches to elicit adjacent neural depolarization, thus avoiding direct neural contact with a stimulating electrode and reducing problems associated with neural inflammation and injury associated with direct contact electrodes.

Implantable Medical Device and Methods

FIG. 1 illustrates a neural stimulator with autonomic balance feedback, according to various embodiments of the present subject matter. The illustrated neural stimulator 100 includes a controller 101 operably connected to neural stimulator circuitry 102 to generate a neural stimulation signal 103 to stimulate neural target(s) in a neural network 104. Embodiments deliver the neural stimulation to the neural target(s) through at least one electrode positioned proximate to the neural target. Other embodiments use other energy waves, such as ultrasound and light energy waves, to stimulate the neural target. The illustrated neural stimulator 100 includes a heart rate detector 105. A heart rate detector embodiment includes sensors to detect R-waves in a cardiogram, and circuitry to determine the R-R interval. Examples of sensors capable of being used to detect R-waves include leads in or around the heart, and a leadless ECG which includes electrodes on a housing of the implantable device that sense volume-conducted cardiac electrical signals. Various embodiments include a PVC sensor 106, various embodiments include a PVC stimulator 107, and various embodiments include both a PVC sensor and a PVC stimulator. A PVC sensor can sense an intrinsic or induced PVC. An example of a PVC stimulator is a stimulator adapted to pace the right ventricle (RV). The illustrated neural stimulator 100 includes a PVC event detector 108, which receives inputs from the PVC stimulator 107 and the PVC sensor 106 to determine when a PVC event occurs. The PVC event detector can receive a signal from the PVC stimulator indicating that a PVC stimulation was provided, and/or can sense and confirm that a PVC actually occurred in response to the PVC stimulation.

The illustrated neural stimulator 100 includes an analyzer 109 that receives heart rate data 110 from the heart rate detector, and receives a signal 111 from the PVC event detector that indicates when a PVC event occurs. The analyzer is adapted to process this information to determine an Autonomic Balance Indicator (ABI) 112. The ABI is processed as a function of the heart rate before the PVC event and the heart rate after the PVC event. In various embodiments, the ABI values include the HRT values TO and TS. In various embodiments, these ABI values 112 are received by the controller 101 for use in titrating the neural stimulation delivered by the neural stimulator circuitry 102. In various embodiments, the ABI values are received by a controller to verify capture; and the controller adjusted neural stimulation parameters/neural stimulation locations as part of an auto-capture process until the ABI values indicate the desired neural stimulation result.

The illustrated neural stimulator 100 also includes sensor circuitry 113, a clock 114, memory 115, and a transceiver 116. The sensor circuitry 113 can include various sensors to sense neural stimulation, sensors to sense surrogates of neural stimulation, or sensors to further identify the physiological state of the patient such as respiratory and activity sensors. The clock 114 can be used by the controller 101 to enable the appropriate circuitry to enable an ABI analysis. Various embodiments analyze ABI periodically at or about equal time intervals, and various embodiments analyze ABI intermittently at non-equal time intervals. Some embodiments analyze ABI on demand as part of a user-controller programmer system and some embodiments are synchronized with neural stimulation "on" and/or neural stimulation "off" as part of a neural stimulation threshold application. For example, some embodiments trigger the ABI analysis upon the detection of an event, and some embodiments trigger the ABI at predetermined times within the neural stimulation therapy. In response to a trigger, the controller enables ABI at 117, which enables the heart rate tracker to detect the heart rate (e.g. R-R intervals). After a delay 118, the ABI enable signal enables the PVC sensor 106 to begin sensing for a PVC. The controller 101 can also generate a PVC stimulation signal at 119 after an appropriate delay 120 after generating the ABI signal. The delay 118 and the delay 120 do not need to be the same delay. For example, some embodiments will sense for a PVC for a predetermined amount of time before generating a PVC stimulation signal. The delays 118 and 120 are provided to allow the heart rate detector to collect the pre-PVC heart rate data before a PVC can be detected and processed. The enable signal can be terminated after the analyzer has the data required to generate the ABI value. The memory 115 can store instructions operated on by the controller 101 to deliver the neural stimulation and analyze the ABI to titrate the neural stimulation. The memory can also store the ABI values 121 and a time stamp 122 associated with each ABI value. A collection of these discrete measurements can be processed to determine the appropriate adjustments for the neural stimulation. Various embodiments adjust the amplitude, frequency, burst frequency, morphology, pulse width or various combinations thereof of the stimulation signal. The burst frequency can be adjusted by adjusting the burst duration and/or the duty cycle of the signals. The controller also can send results to the programmer for physician action, including reprogramming the neural stimulator or accepting settings used in a threshold test. The transceiver 116 is used to communicate with another device, such as an external programmer. Programming instructions can be communicated to the device through the transceiver. Additionally, the transceiver is used to transmit device data and collected data from the neural stimulator to the other device.

FIG. 1 illustrates separate modules to illustrate certain functions performed by the device. It is understood that certain of the illustrated modules can be combined. Thus, for example, the controller 101 and analyzer 109 can function together as a process or module to perform TO and TS calculations, and to perform trending functions to determine when the quantified autonomic balance indicates that the neural stimulation should be adjusted.

Figure 2A:
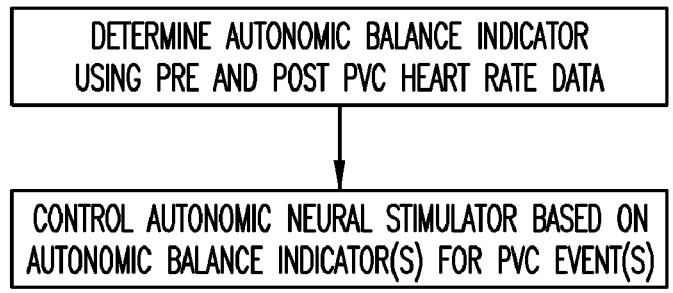
FIGS. 2A and 2B illustrate an embodiment to control autonomic neural stimulation and an embodiment to determine neural stimulation capture, respectively, according to various embodiments of the present subject matter.
Figure 2B:
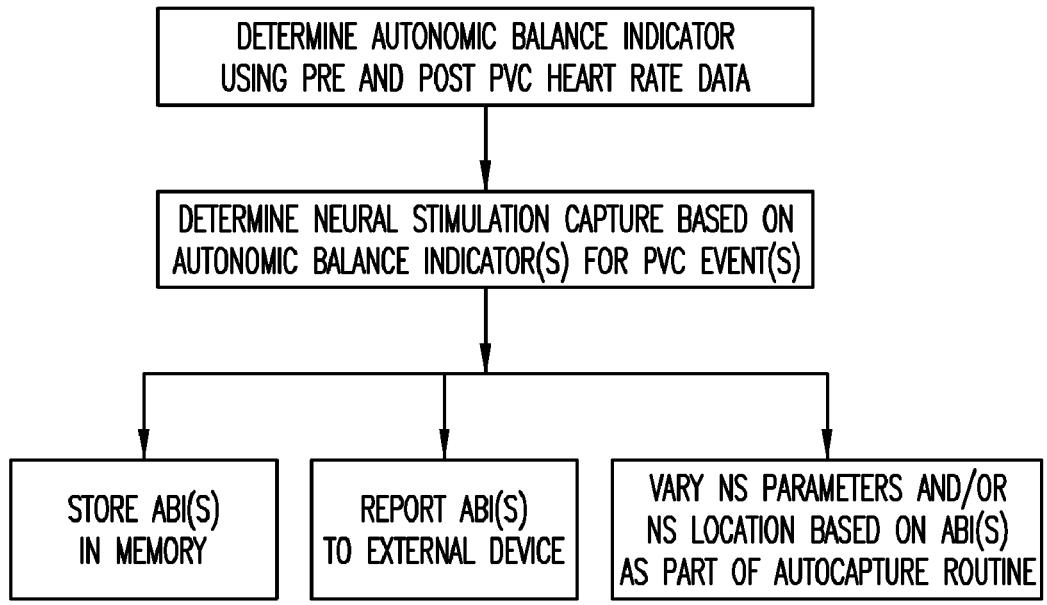

FIGS. 2A and 2B illustrate an embodiment to control autonomic neural stimulation and an embodiment to determine neural stimulation capture, respectively, according to various embodiments of the present subject matter. With reference to the method illustrated in FIG. 2A, an autonomic balance indicator (ABI) is determined using pre and post-PVC heart rate data, and an autonomic neural stimulator is controlled based on at least one ABI of at least one induced or intrinsic PVC event. With reference to the method illustrated in FIG. 2B, an ABI is determined using pre and post-PVC heart rate data, and neural stimulation capture is determined based on at least one ABI for at least one induced or intrinsic PVC event. The ABI measurement(s) can be stored in memory of the implantable medical device, can be reported to an external device such as a programmer, or can be used to vary the neural stimulation parameters and/or neural stimulation locations based on ABI(s) as part of an auto-capture routine.

Figure 2C:
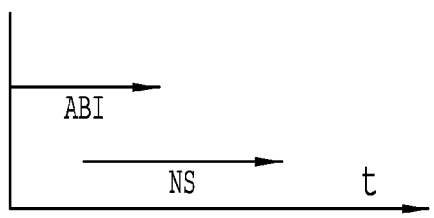
FIGS. 2C-2E illustrate timing diagrams for embodiments of the present subject matter.
Figure 2D:
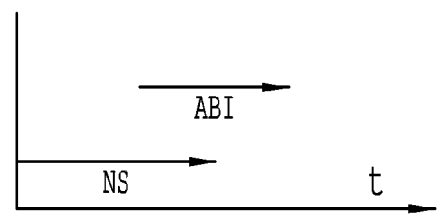
Figure 2E:
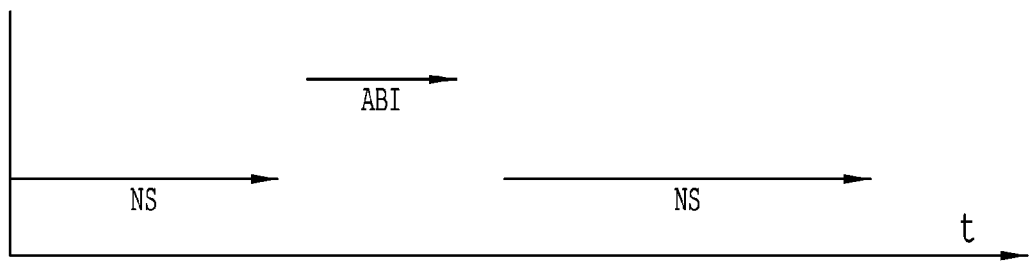

FIGS. 2C-2E illustrate timing diagrams for embodiments of the present subject matter. FIG. 2C illustrates an embodiment in which ABI is being determined at the time neural stimulation is applied; and FIG. 2D illustrates an embodiment in which ABI is determined at the end of neural stimulation. These embodiments permit the detection of ABIs that correspond to time periods with and without neural stimulation. Such embodiments may be useful to detect acute evoked responses to ABI. FIG. 2E illustrates an embodiment in which a neural stimulation therapy is interrupted to perform an ABI measurement. Such an embodiment may be useful to detect a steady-state autonomic balance.

Figure 2F:
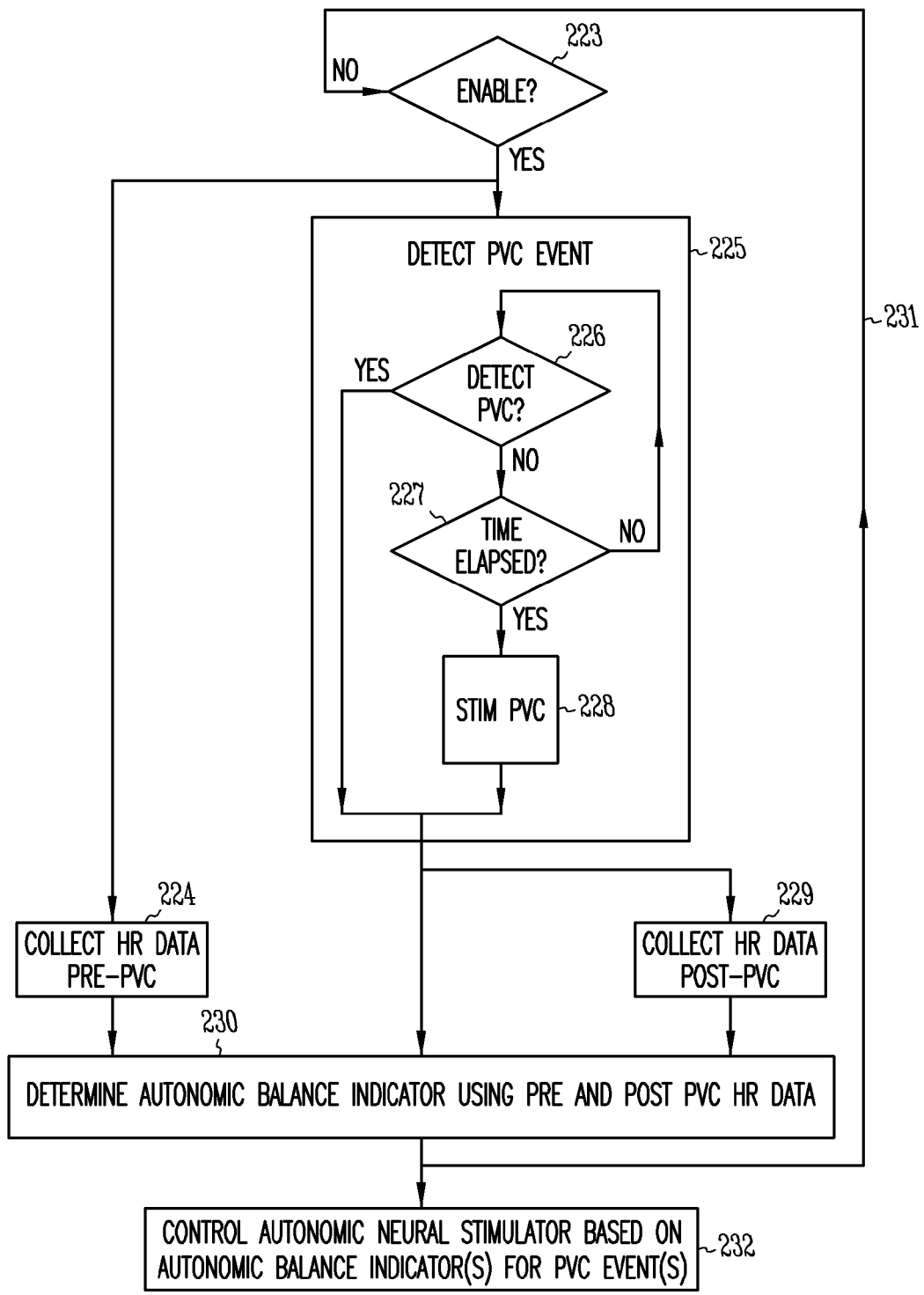
FIG. 2F illustrates a method for determining an autonomic balance indicator for use in controlling an autonomic neural stimulator, according to various embodiments of the present subject matter.

FIG. 2F illustrates a method for determining an autonomic balance indicator for use in controlling an autonomic neural stimulator, according to various embodiments of the present subject matter. At 223, it is determined whether an enable signal has been received. In response to an enable signal, pre-PVC heart rate data is collected at 224. After initial pre-PVC heart rate data is collected, the process detects a PVC event at 225. The pre-PVC heart rate data 224 continues be collected until the PVC event 225 is detected. Various embodiments only detect intrinsic PVCs, various embodiments only induce or stimulate PVCs, and various embodiments perform a process to detect intrinsic PVCs, and stimulate PVCs. For example, in the illustrated embodiment, a process is performed to detect PVCs at 226. If a PVC is not detected at 226 and if a predetermined time has elapsed at 227, then a PVC is induced at 228. After an acceptable PVC occurs, post-PVC heart rate data is collected at 229. At 230, the process determines an autonomic balance indicator (ABI) using the pre-PVC heart rate data and the post-PVC heart rate data. As illustrated by line 231, the process can be repeated to collect additional ABIs. At 232, the autonomic neural stimulator is controlled based on the calculated ABI(s) for the PVC event(s).

Figure 3:
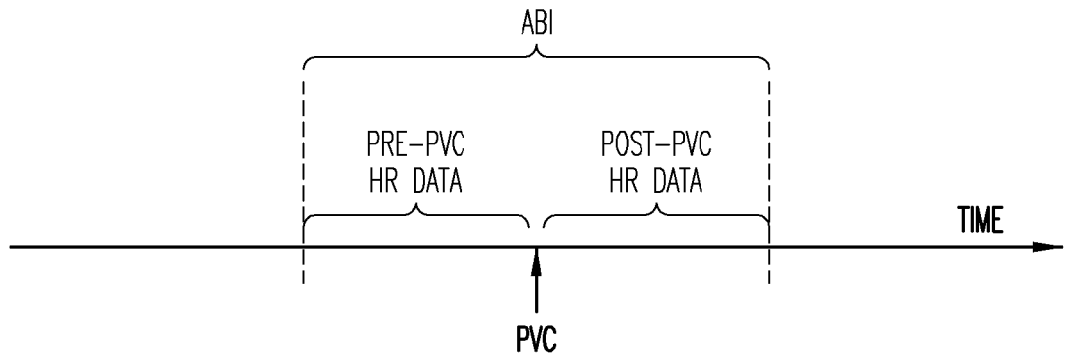
FIG. 3 illustrates a timeline with a PVC event, pre-PVC heart rate data, and post-PVC heart rate data, according to various embodiments of the present subject matter.

FIG. 3 illustrates a timeline with a PVC event, pre-PVC heart rate data, and post-PVC heart rate data. As illustrated in the figure, an ABI value is determined by pre-PVC heart rate data and post-PVC heart rate data. According to various embodiments, the illustrated pre-PVC heart rate data includes a predetermined number of R-R intervals (e.g. 2 beats) that immediately precede the PVC event; and the illustrated post-PVC heart rate data includes a predetermined number of R-R intervals (e.g. 2 beats) that immediately follow the PVC event. Also, ABI can be measured periodically or intermittently and recorded, without necessarily resulting in a neural stimulation level adjustment.

Figure 4:
FIG. 4 illustrates a timeline where ABIs are periodically determined at discrete times, according to various embodiments of the present subject matter.

FIG. 4 illustrates a timeline where ABIs are periodically determined at discrete times. The ABIs have been illustrated in FIG. 3. As illustrated in FIG. 4, the ABIs are determined at relatively constant time intervals. For example, and not by way of limitation, an ABI can be determined at or about every hour, or every day or at any other appropriate interval to titrate the autonomic neural therapy. It is noted that, for some embodiments, it may take some time before an acceptable intrinsic PVC is detected for use in determining the ABI.

Figure 5:
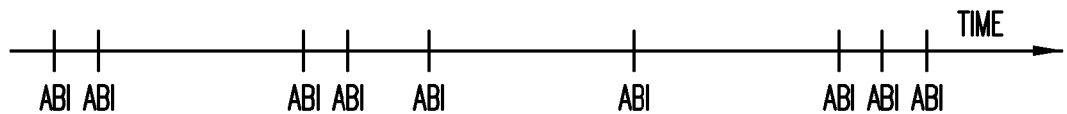
FIG. 5 illustrates a timeline where ABIs are intermittently determined at discrete times, according to various embodiments of the present subject matter.

FIG. 5 illustrates a timeline where ABIs are intermittently determined at discrete times. The time intervals between ABIs are not equal. These time intervals can be preprogrammed based on a clock or can otherwise be triggered.

Figure 6:
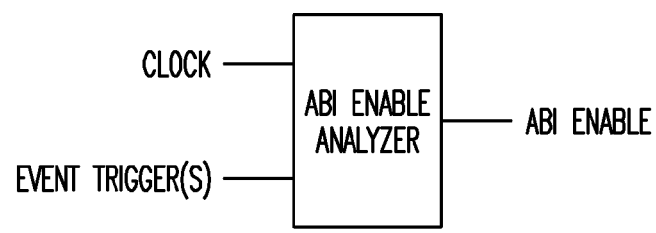
FIG. 6 illustrates a logic circuit for use to trigger an analysis of an ABI, according to various embodiments of the present subject matter.

FIG. 6 illustrates a logic circuit for use to trigger an analysis of an ABI, according to various embodiments of the present subject matter. The ABI enable analyzer can be formed as part of the controller 101 in FIG. 1, for example. The illustrated ABI enable analyzer receives inputs from a clock and from event trigger(s). The event trigger(s) can be based on sensor data or changes in neural stimulation therapy or CRM therapy or programmer signal, for example. The ABI enable signal is generated based on the time or detected event trigger(s).

Figure 7:
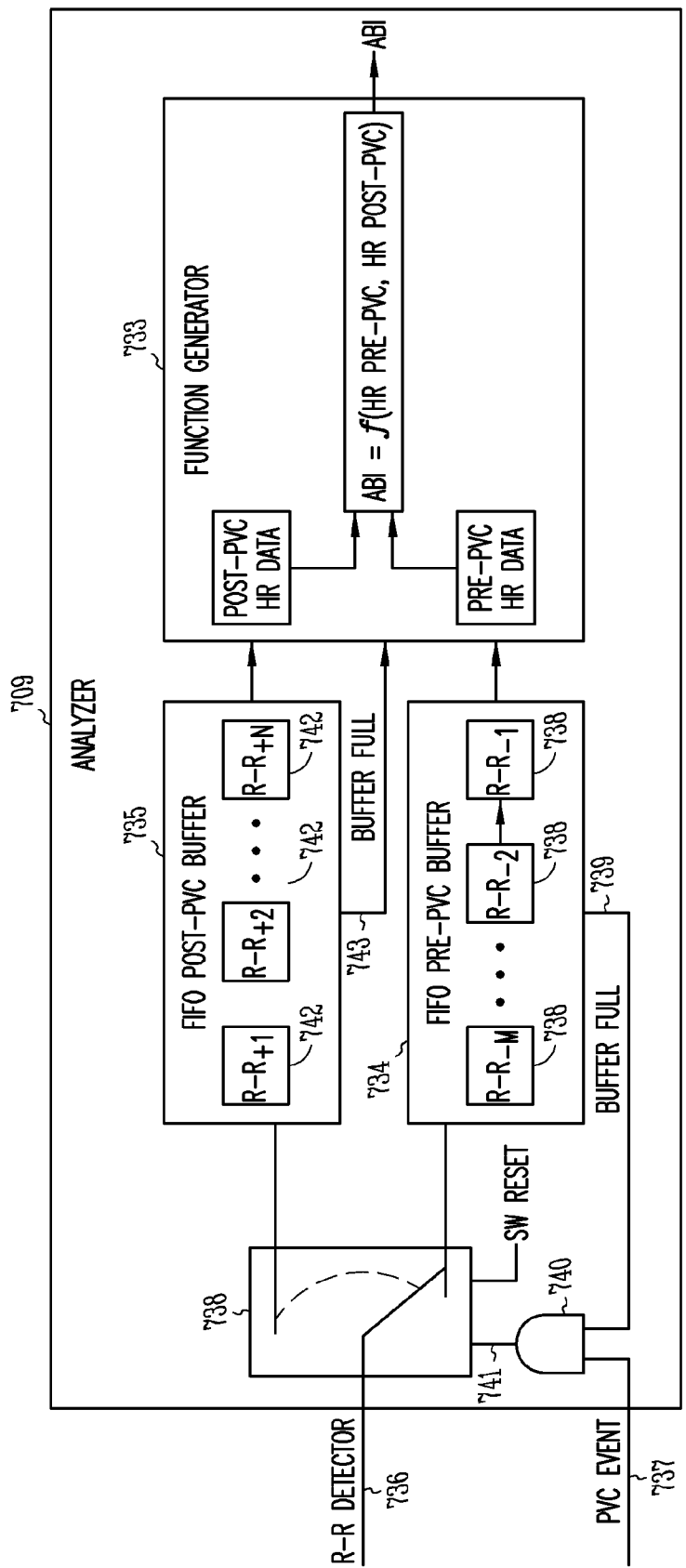
FIG. 7 illustrates an analyzer, such as illustrated in FIG. 1, according to various embodiments of the present subject matter.

FIG. 7 illustrates an analyzer, such as illustrated at 109 in the neural stimulator device 100 of FIG. 1, according to various embodiments of the present subject matter. The illustrated analyzer 709 includes a function generator 733, a first-in, first-out (FIFO) pre-PVC buffer 734, a FIFO post-PVC buffer 735, an R-R detector input 736, and a PVC event detector input 737. When first enabled, successive R-R intervals are stored via switch 738 into the FIFO pre-PVC buffer 734. The buffer 734 can include different numbers of registers 738 to store the R-R intervals. For example, one embodiment includes two registers adapted to store two consecutive R-R intervals, and one embodiment includes five registers adapted to store five consecutive R-R intervals. Once the buffer 734 is full, the oldest R-R interval is removed from the buffer when the next R-R interval is received. Thus, the buffer stores a sequence of the latest R-R intervals such that, upon a PVC event, the buffer stores the intervals immediately preceding the PVC event. Additionally, an enable signal 739 is generated after the pre-PVC buffer is full, which indicates that the analyzer is ready to process a PVC event. As illustrated by the AND logic gate 740, when the PVC event occurs and the enable signal is present, a signal 741 is generated to actuate the switch 738 and store subsequent R-R intervals in the FIFO post-PVC buffer 735. The buffer 735 can include different numbers of registers 742 to store the R-R intervals. For example, one embodiment includes two registers adapted to store two consecutive R-R intervals, and one embodiment includes five registers adapted to store five consecutive R-R intervals. When the buffer is full, the function generator 733 responds to an enable signal 743 to use the pre-PVC heart rate data stored in the pre-PVC buffer and the post-PVC heart rate data stored in the post-PVC buffer to generate an ABI value. The switch can be reset to begin to receive R-R intervals in the pre-PVC buffer in response to the next ABI enable signal.

Figure 8:
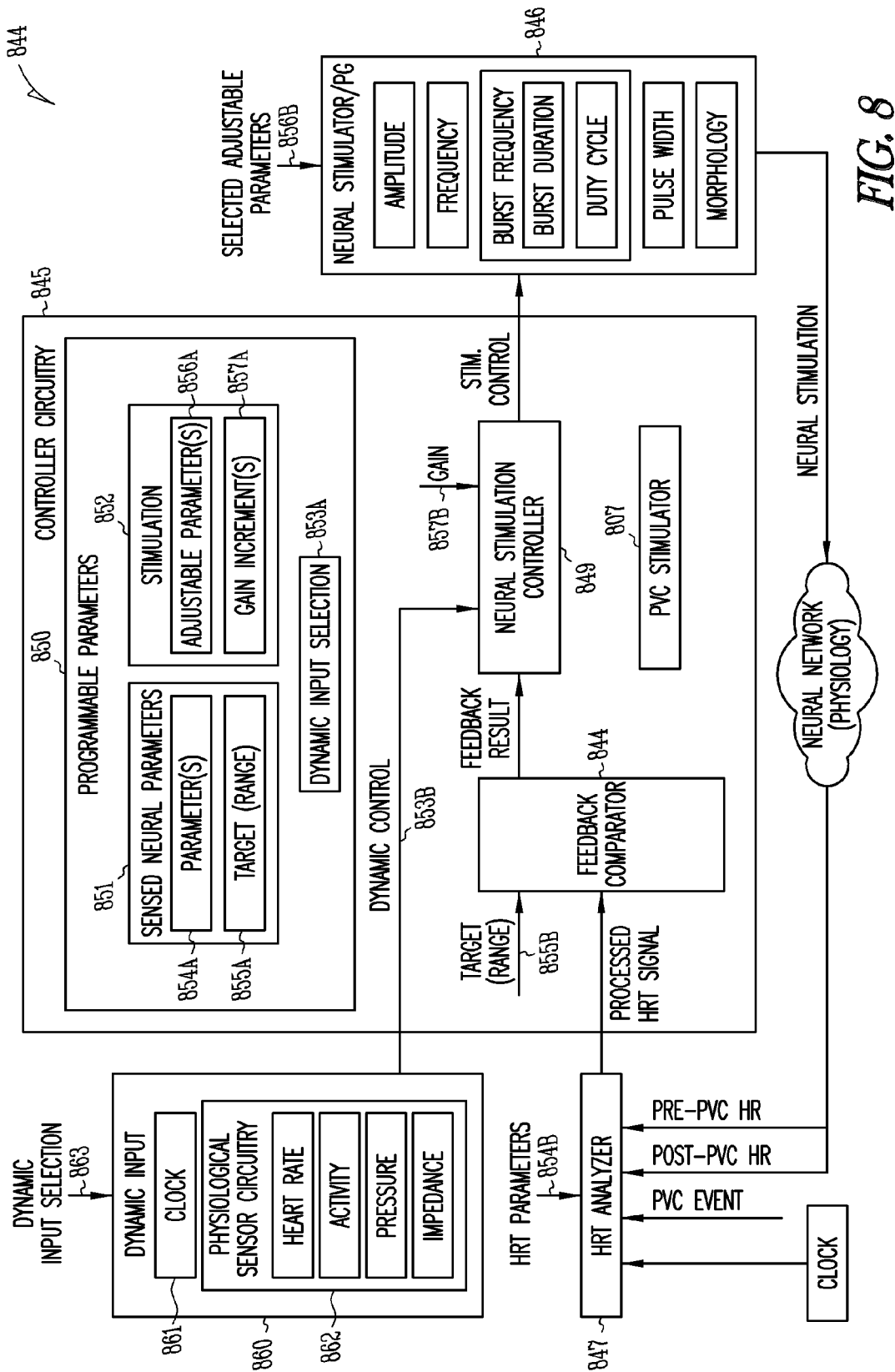
FIG. 8 illustrates an embodiment of a control system for an embodiment of an implantable medical device (IMD) which monitors the autonomic nervous system (ANS) to control neural stimulation of a neural target within the ANS.

FIG. 8 illustrates an embodiment of a control system for an embodiment of an implantable medical device (IMD) which monitors the autonomic nervous system (ANS) to control neural stimulation of a neural target within the ANS. The IMD includes controller circuitry 845, a neural stimulator 846 which can also be referred to as a pulse generator, and an HRT analyzer 847. The illustrated controller 845 includes a feedback comparator 844 which can be referred to as an error detector, and a neural stimulation controller 849.

The illustrated controller circuitry 845 also includes a memory or register 850 where values for various parameters can be programmed by an external programmer using a transceiver. Various embodiments allow one or more of the following parameter types to be programmed: HRT parameters 851, stimulation parameters 852, and dynamic input selection 853A. The illustrated HRT parameters include programmed parameters 854A for low and high thresholds for R-R intervals and other parameters used to determine whether to accept a PVC as a PVC event, and a desired target parameter (or desired range of parameters) 855A. The illustrated stimulation parameters 852 include stimulation parameter(s) to be adjusted 856A in response to a feedback control signal, and available gain increment(s) 857A for the adjustable stimulation parameter(s). These programmable parameters illustrated in memory 850 provide control inputs to various modules of the device. In the illustrated embodiment, the programmable HRT parameter(s) 854A provide a control signal 854B to the HRT analyzer 847 for use in adjusting the way in which the HRT values are calculated. The programmable adjustable stimulation parameters 856A provide a control signal 856B to the neural stimulator 846 that indicates the parameters of the stimulation waveform to be adjusted. The programmable target 855A provides a control signal 855B to the feedback comparator 844, the programmable gain increment 857A provides a control signal 857B to the neural stimulator controller 849 that indicates an appropriate gain (positive and negative) to increment or decrement the stimulation intensity resulting from the stimulation values for the neural stimulation parameter(s). The programmable dynamic input selection 853A provides a control signal 853B to the neural stimulation controller to dynamically adjust the target range to account for other factors such as activity or time.

The HRT analyzes the heart rate, reflective of the health of the autonomic neural network, at time generally corresponding to the PVC events. The illustrated HRT analyzer 847 responds to a PVC event by processing pre-PVC heart rate data and post-PVC heart rate data to determine HRT data, which are output as the processed HRT signal. A clock or timer can be used to determine when to perform HRT analysis. The feedback comparator 844 compares the HRT values (e.g. TO/TS) to the target parameter or target parameter range 855B for the sensed parameter(s). A result of the comparison is provided from the comparator 844 to the neural stimulation controller 849 via a feedback result signal. The controller 849 receives the feedback result signal, and delivers a stimulation control signal to the neural stimulator 846 based on the feedback result signal. The neural stimulator 846 receives the stimulation control signal and controls the neural stimulation to adjust the intensity of stimulation if appropriate to converge to the desired HRT data as reflected by the comparison of processed HRT signal to the target 855B. According to various embodiments, the stimulator circuitry 846 includes modules to set or adjust any one or any combination of two or more of the following pulse features: the amplitude of the stimulation pulse, the frequency of the stimulation pulse, the burst frequency of the pulse, the wave morphology of the pulse, and the pulse width. The illustrated burst frequency pulse feature includes burst duration and duty cycle, which can be adjusted as part of a burst frequency pulse feature or can be adjusted separately without reference to a steady burst frequency.

In addition to the feedback result control input signal, some embodiments of the neural stimulation controller 849 also receive a gain control input signal 857B used to provide the desired stimulation control signal to the neural stimulator 846. It is noted that the intensity of the neural stimulation signal can be complexly related to the parameters of the stimulation signal. Generally, an increased amplitude of the signal increases neural stimulation. Additionally, there is a frequency window which corresponds to the highest neural stimulation intensity, and frequencies that are either higher or lower than the frequency window provide less neural stimulation. Also, stimulated neural sites can quickly adapt to steady stimulation. Thus, adjustments in stimulation intensity can correspond to a variety of adjustments to one or more of the amplitude of the stimulation pulse, the frequency of the stimulation pulse, the burst frequency of the pulse, the burst duration of the pulse, the duty cycle of the stimulation, the wave morphology of the pulse, and the pulse width. The gain control adjusts the stimulation parameter(s) to achieve a desired increment or decrement in neural stimulation intensity. According to some embodiments, the parameter adjustments are predetermined to provide the stimulation intensity adjustments. Some embodiments use an iterative protocol to determine the effects that parameter change(s) have on intensity. For example, according to some embodiments, the gain control signal 857B controls an algorithm used to methodically adjust stimulation parameter(s) that are available for adjustment, compare the result to determine if the neural stimulation results in a result closer to the target or further from the target, and then adjust the stimulation parameter(s) again to achieve the desired increment or decrement in the neural response. The same or different parameters can be adjusted to achieve the desired response.

In addition to the feedback result control input signal, some embodiments of the neural stimulation controller 849 also receive a dynamic control input signal used to provide the desired stimulation control signal. The illustrated dynamic input 860 includes a clock 861 and physiological sensor circuitry 862. The illustrated physiological sensor circuitry includes a heart rate sensor, an activity sensor, a pressure sensor, and impedance sensor. Other physiological sensors can be used. The dynamic input 863 enables the dynamic adjustment of the effective operating target or target range based on a clock (e.g. a circadian rhythm) and/or based on physiological parameters. Thus, for example, the dynamic input allows the target for the HRT values to be different for someone exercising in the afternoon than sleeping in the middle of the night, or can otherwise adjust the algorithms used to calculate the HRT values. The dynamic input can be used in other applications. The selection of the dynamic input as well as the resulting control algorithms that use the dynamic input control signal can be programmable. The illustrated controller circuitry 845 also includes a PVC stimulator 807, such as illustrated at 107 in FIG. 1.

Figure 9A:
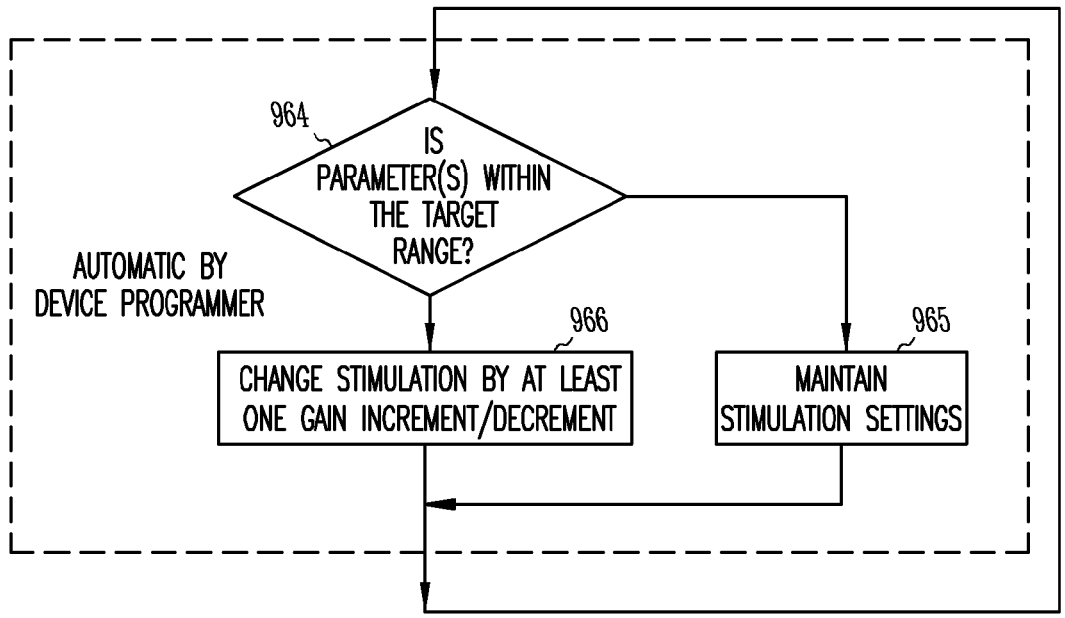
FIG. 9A illustrates an embodiment of a method to adjust neural stimulation based on sensed parameter(s), such as may be performed by an implantable medical device (IMD) or programmer, for example.

FIG. 9A illustrates an embodiment of a method to adjust neural stimulation based on sensed parameter(s), such as may be performed by an implantable medical device (IMD) or programmer, for example. At 964, a determination is made as to whether the sensed parameter(s) are within the target range. The sensed parameter(s) include HRT values (e.g. TO, TS). If the parameter(s) are determined to be within a target range, the stimulation settings are maintained 965 and the process returns to 964. If the parameter(s) are determined to be outside of a target range, the process proceeds to 966 to change the neural stimulation by at least one gain increment or decrement, depending on the arrangement, to move the sensed parameter(s) toward the target. Various embodiments provide other ranges above and/or below the target range; various embodiments provide a target-sub-range within the target range, and various embodiments further provide a number of other sub-ranges above and/or below the target sub-range; various embodiments provide a target sub-sub-range within a target sub-range, and various embodiments further provide other sub-sub-ranges above and/or below the target sub-sub-range. Various stimulation adjustment protocols (e.g. gain) can be used depending on the range, sub-range and sub-sub-range. Thus, for example, large adjustments can be made by adjusting one parameter (e.g. frequency) of the stimulation signal, and smaller adjustments can be made by adjusting another parameter (e.g. amplitude) of a stimulation signal. Such a method can use ABI(s) to titrate chronic neural stimulation or perform a neural stimulation auto-capture threshold test.

Figure 9B:
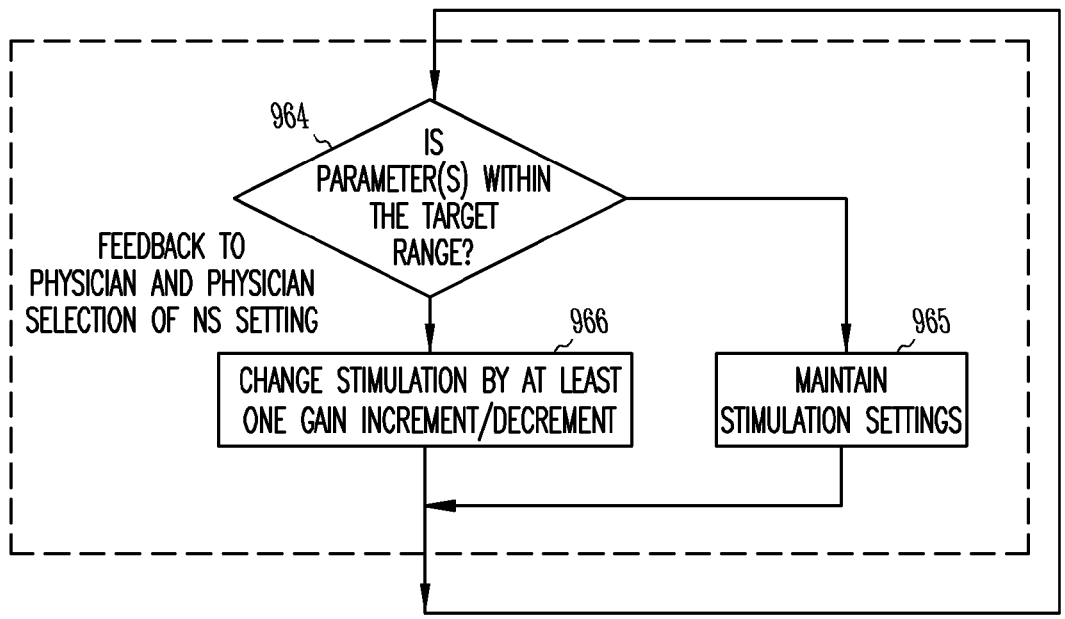
FIG. 9B illustrates an embodiment of a method to adjust neural stimulation based on sensed parameter(s) reported to a physician for use by the physician to select a neural stimulation setting, for example.

FIG. 9B illustrates an embodiment of a method to adjust neural stimulation based on sensed parameter(s) reported to a physician for use by the physician to select a neural stimulation setting, for example. The method is similar to FIG. 9A, except that the ABI(s) are communicated to the physician, and the physician analyzes the data to determine whether and how to change the stimulation.

Figure 10:
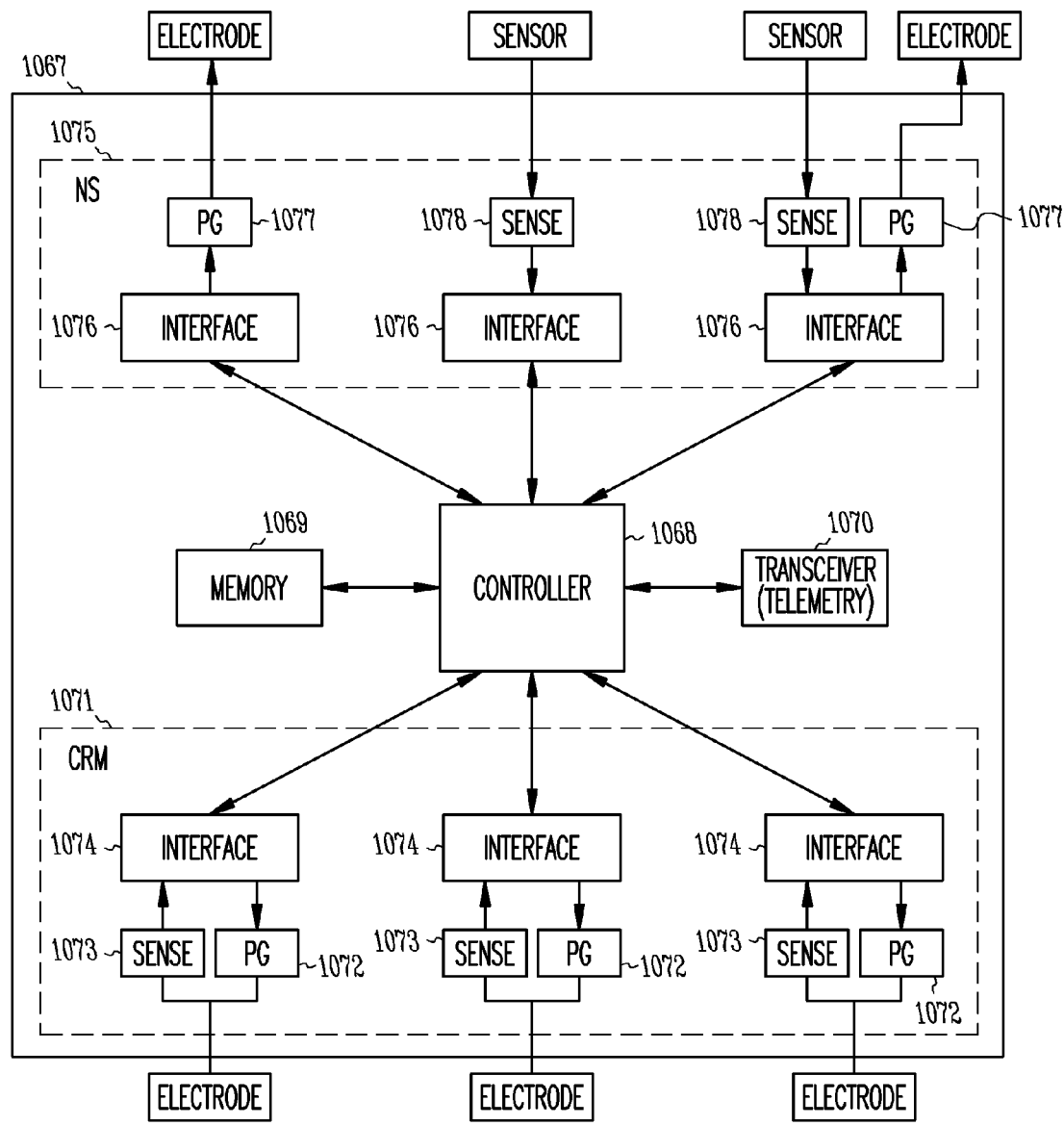
FIG. 10 illustrates an implantable medical device (IMD) having a neural stimulator (NS) component and cardiac rhythm management (CRM) component, according to various embodiments of the present subject matter.

FIG. 10 illustrates an implantable medical device (IMD) having a neural stimulator (NS) component and cardiac rhythm management (CRM) component, according to various embodiments of the present subject matter. The illustrated device 1067 includes a controller 1068 and a memory 1069. According to various embodiments, the controller 1068 includes hardware, software, or a combination of hardware and software to perform the neural stimulation and CRM functions. Examples of CRM functions include, for example, pacing, defibrillating, and cardiac resynchronization therapy (CRT) functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. The illustrated device 1067 further includes a transceiver 1070 and associated circuitry for use to communicate with a programmer or another external or internal device. Various embodiments include a telemetry coil.

The CRM therapy section 1071 includes components, under the control of the controller, to stimulate a heart and/or sense cardiac signals using one or more electrodes. The CRM therapy section includes a pulse generator 1072 for use to provide an electrical signal through an electrode to stimulate a heart, and further includes sense circuitry 1073 to detect and process sensed cardiac signals or otherwise detect heart rate parameters according to the present subject matter. Thus, for example, sense circuitry 1073 can be used to detect a PVC and to detect R-R intervals, and the pulse generator 1072 can be used to induce a PVC. An interface 1074 is generally illustrated for use to communicate between the controller 1068 and the pulse generator 1072 and sense circuitry 1073. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 1075 includes components, under the control of the controller, to stimulate neural target(s) and sense ANS parameters associated with nerve activity, and in some embodiments sense surrogates of ANS parameters such as blood pressure and respiration. Examples of NS therapy include, but are not limited to, therapies to treat hypertension, epilepsy, obesity and breathing disorders. Three interfaces 1076 are illustrated for use to provide ANS therapy. However, the present subject matter is not limited to a particular number interfaces, or to any particular stimulating or sensing functions. Pulse generators 1077 are used to provide electrical pulses to an electrode for use to stimulate a neural target. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1078 are used to detect and process signals from a sensor, such as a sensor of nerve activity, pulsatile parameters, blood pressure, respiration, and the like. The interfaces 1076 are generally illustrated for use to communicate between the controller 1068 and the pulse generator 1077 and sense circuitry 1078. Each interface, for example, may be used to control a separate lead. Various embodiments of the NS therapy section only include a pulse generator to stimulate a neural target.

Figure 11:
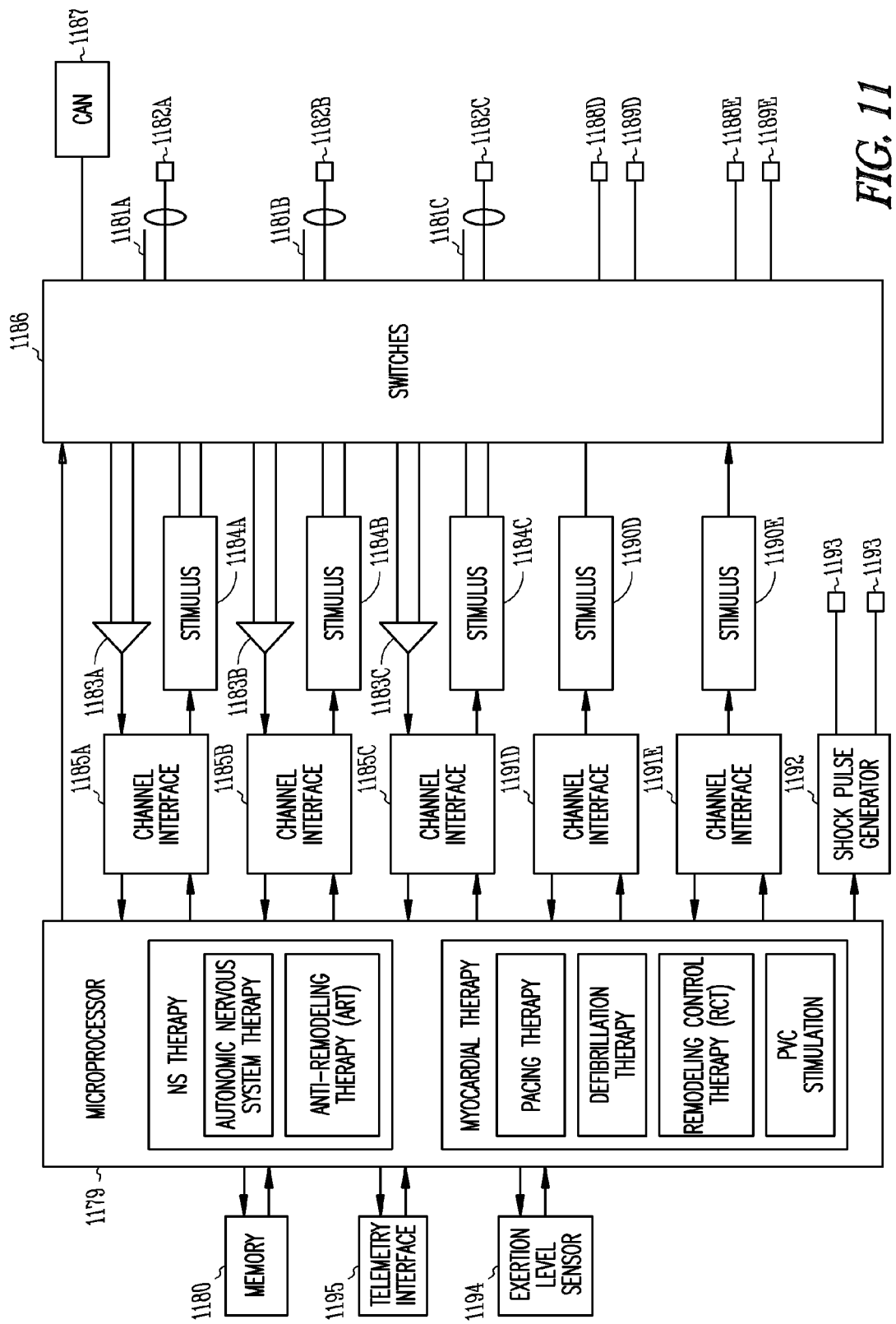
FIG. 11 shows a system diagram of an embodiment of a microprocessor-based implantable device.

FIG. 11 shows a system diagram of an embodiment of a microprocessor-based implantable device. The device is equipped with multiple sensing and pacing channels which may be physically configured to sense and/or pace multiple sites in the atria or the ventricles, and to provide neural stimulation. The illustrated device can be configured for myocardial stimulation (pacing, defibrillation, CRT/RCT) and neural stimulation (therapy of sleep disordered breathing, CRM, CRT/ART). The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The ventricle pacing channel(s) can be used to induce a PVC and the ventricle sensing channel(s) can be used to sense a PVC and sense R-R intervals. The controller 1179 of the device is a microprocessor which communicates with memory 1180 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor.

Shown in FIG. 11, by way of example, are three sensing and pacing channels, such as can be used to provide myocardial stimulation/pacing, designated "A" through "C" comprising bipolar leads with ring, or proximal, electrodes 1181A-C and distal, or tip, electrodes 1182A-C, sensing amplifiers 1183A-C, pulse generators 1184A-C, and channel interfaces 1185A-C. Each channel thus includes a pacing channel made up of the pulse generator connected to the electrode and a sensing channel made up of the sense amplifier connected to the electrode. The channel interfaces 1185A-C communicate bidirectionally with the microprocessor 1179, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a switching network 1186 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring, or proximal, and tip, or distal, electrodes of a lead or in a unipolar mode using only one of the electrodes of the lead with the device housing or can 1187 serving as a ground electrode.

Also shown in FIG. 11, by way of example, are nerve stimulation channels designated "D" and "E." Neural stimulation channels are incorporated into the device. These channels can be used to deliver neural stimulation, such as for ART as part of CRT. The illustrated channels include leads with electrodes 1188D and 1189D and electrodes 1188E and 1189E, a pulse generator 1190D and 1190E, and a channel interface 1191D and 1191E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology, for example.

A shock pulse generator 1192 is also interfaced to the controller for delivering a defibrillation shock via a pair of shock electrodes 1193 to the atria or ventricles upon detection of a shockable tachyarrhythmia.

The illustrated controller includes a module for controlling neural stimulation (NS) therapy and module for controlling myocardial therapy. As illustrated, the NS therapy module includes a module for performing an autonomic neural stimulation. Also as illustrated, the myocardial therapy module includes a module for controlling pacing therapies, a module for controlling defibrillation therapies, and a module for stimulating a PVC. The illustrated controller is also adapted to control CRT by controlling RCT (a myocardial stimulation therapy), and in some embodiments by controlling ART (a neural stimulation therapy).

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 1194 (e.g., an accelerometer, a minute ventilation sensor, or other sensor that measures a parameter related to metabolic demand) enables the controller to adapt the pacing rate in accordance with changes in the patient's physical activity and can enable the controller to modulate the delivery of neural stimulation and/or cardiac pacing. A telemetry interface 1195 is also provided which enables the controller to communicate with an external programmer or remote monitor.

Systems with IMD

Figure 12:
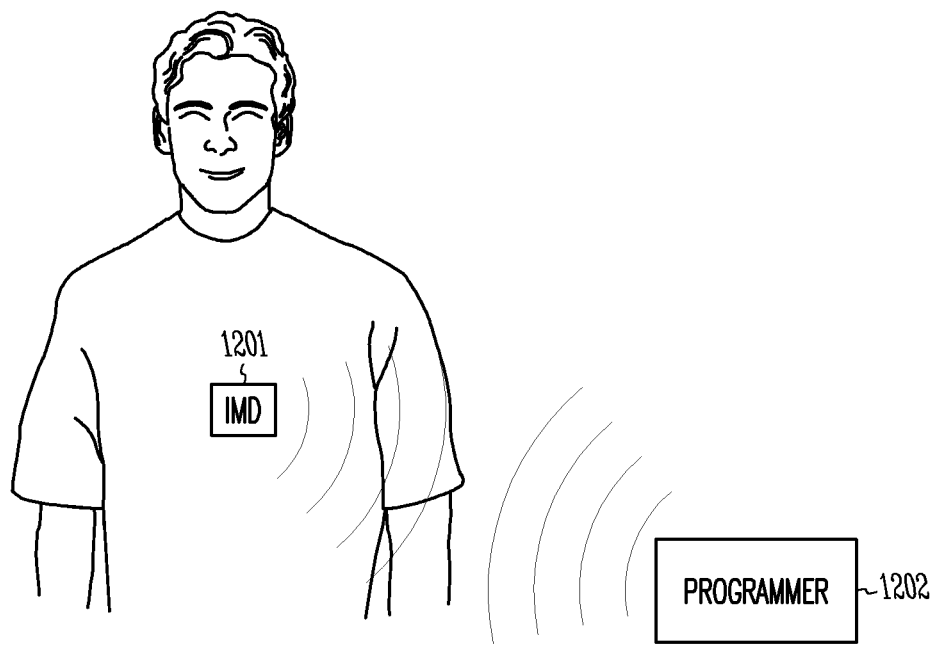
FIGS. 12-15 generally illustrate examples of systems that include an implantable neural stimulator with autonomic balance feedback determined using a PVC, according to various embodiments.
Figure 13:
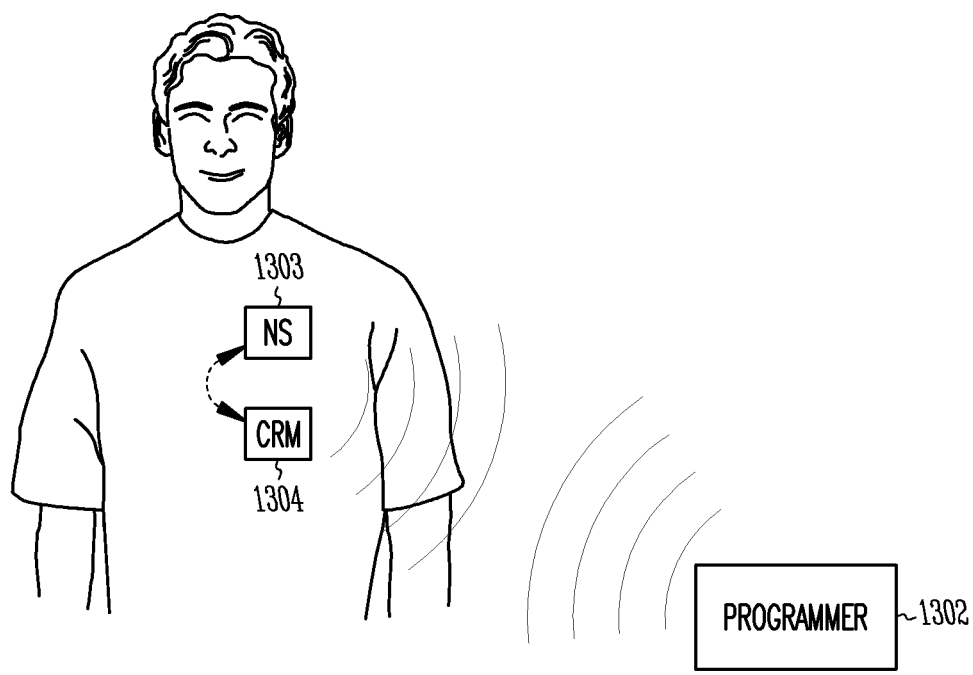

FIGS. 12-15 generally illustrate examples of systems that include an implantable neural stimulator with autonomic balance feedback determined using a PVC, according to various embodiments. FIG. 12 illustrates a system embodiment with an IMD 1201 and programmer 1202 capable of wirelessly communicating with the IMD 1201. Thus, the programmer can be used to adjust the programmed therapy provided by the IMD, and the IMD can report device data (such as battery and lead resistance) and therapy data (such as sense and stimulation data) to the programmer using radio telemetry, for example. The illustrated IMD can include both neural stimulation capabilities with autonomic balance feedback and CRM capabilities, as discussed within this disclosure. The system illustrated in FIG. 12 can also be used for neural stimulation threshold measurement. FIG. 13 illustrates a system embodiment with an implantable neural stimulator 1303, an implantable CRM device 1304, and a programmer 1302 capable of wirelessly communicating with at least one of the neural stimulator 1303 and CRM device 1304. Thus, the programmer can be used to adjust the programmed therapy provided by the devices, and the devices can report device data (such as battery and lead resistance) and therapy data (such as sense and stimulation data) to the programmer using radio telemetry, for example. The devices 1303 and 1304 are adapted to communicate with each other to integrate the therapies. For example, the CRM device 1304 can be used to detect and/or induce PVCs, and detect pre-PVC heart rate data and post-PVC heart rate data for use in determining ABIs to appropriately titrate the neural stimulation therapy according to an assessed autonomic balance. HRT calculations can be performed in either device 1303 or 1304. An example of the system illustrated in FIG. 13 includes a programmer serving as a communication link between the neural stimulator and CRM devices. For example, the programmer can set up some neural stimulation parameters, trigger a neural stimulation sequence, instruct the CRM to stimulate a PVC, and measure HRT during the neural stimulation. The HRT data would be returned to the programmer, which then alters the neural stimulation parameters and repeats or programs selected neural stimulation parameters and finishes.

Figure 14:
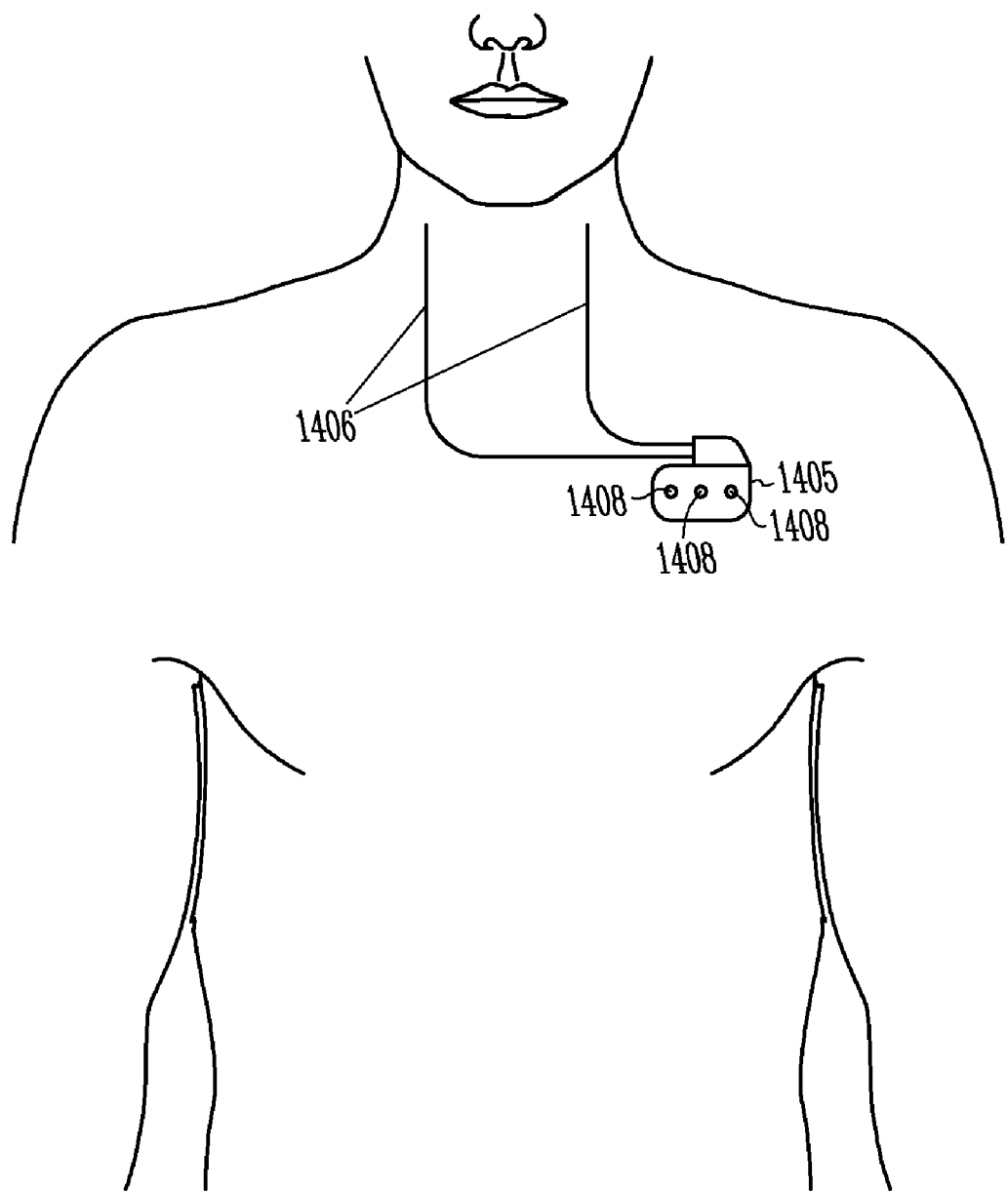

FIG. 14 illustrates a system embodiment in which an IMD 1405 is placed subcutaneously or submuscularly in a patient's chest with lead(s) 1406 positioned to stimulate a vagus nerve. According to various embodiments, neural stimulation lead(s) 1406 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes on the housing of the device. These ECG electrodes 1408 are capable of being used to detect a PVC. Various embodiments include cardiac leads, not illustrated, capable of inducing a PVC. Such cardiac leads can be used to sense PVCs instead of wireless ECGs.

Figure 15:
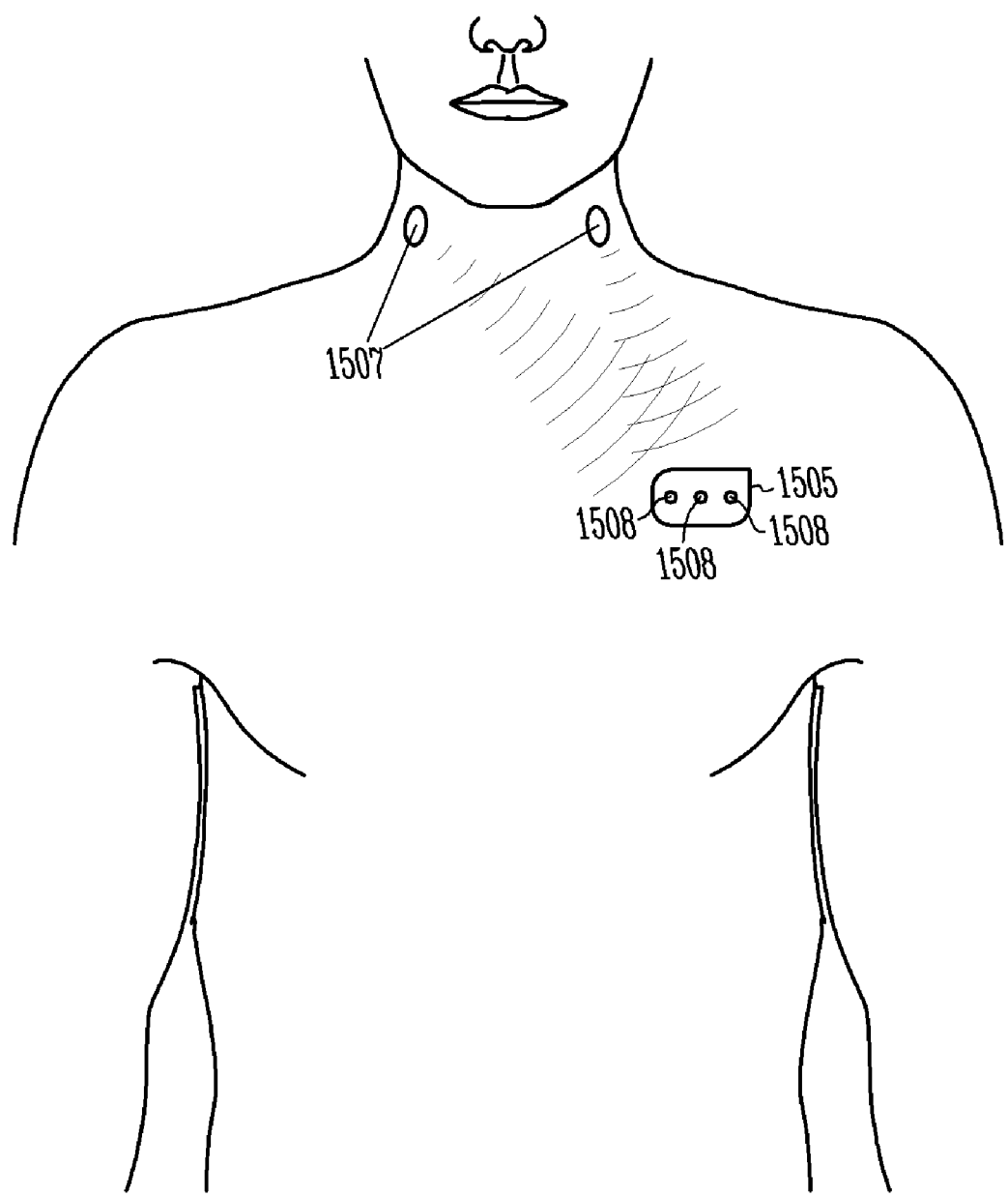

FIG. 15 illustrates a system embodiment that includes an implantable medical device (IMD) 1505 with satellite electrode(s) 1507 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1508 are capable of being used to detect a PVC. Various embodiments include cardiac leads, not illustrated, capable of inducing a PVC. Such cardiac leads can be used to sense PVCs instead of wireless ECGs.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method for modulating autonomic balance between parasympathetic tone and sympathetic tone in an autonomic nervous system (ANS), the method comprising:

stimulating an autonomic neural target to modulate the autonomic balance in the ANS;

performing a neural stimulation threshold test in response to a demand for the neural stimulation threshold test, wherein performing the neural stimulation threshold test includes:

inducing a premature ventricular contraction (PVC) event or detecting an intrinsic PVC event;

detecting pre-PVC heart rate data and post-PVC heart rate data;

measuring heart rate turbulence (HRT) in response to the PVC event using the pre-PVC heart rate data and the post-PVC heart rate data to generate an autonomic balance indicator (ABI); and using the ABI to determine whether the neural stimulation signal evokes a response above a threshold.

2. The method of claim 1, wherein performing a neural stimulation threshold test in response to a demand for the neural stimulation threshold test includes performing the neural stimulation threshold test based on a time trigger.

3. The method of claim 1, wherein performing a neural stimulation threshold test in response to a demand for the neural stimulation threshold test includes performing the neural stimulation threshold test based on a detected event trigger.

4. The method of claim 1, wherein performing a neural stimulation threshold test in response to a demand for the neural stimulation threshold test includes performing the neural stimulation threshold test based on a clinician-generated command.

5. The method of claim 1, further comprising reporting the ABI to a clinician to inform the clinician if the neural stimulation signal evokes a response above the threshold.

6. The method of claim 1, wherein inducing the PVC event includes pacing a ventricle.

7. The method of claim 1, performing the neural stimulation threshold test includes performing a process to detect the intrinsic PVC, and inducing the PVC event if the intrinsic PVC is not detected within a predetermined time.

8. The method of claim 1, wherein using the ABI to determine whether the neural stimulation signal evokes a response above a threshold includes using a plurality of ABIs to determine whether the neural stimulation signal evokes a response above a threshold.

9. The method of claim 1, further comprising performing an autocapture routine to automatically adjust stimulation parameters of the stimulation signal to stimulate the autonomic neural target based on results of the neural stimulation capture test.

10. The method of claim 1, further comprising changing the autonomic neural target to be stimulated based on results of the neural stimulation capture test.

11. The method of claim 1, further comprising changing a stimulation vector based on results of the neural stimulation capture test.

12. The method of claim 1, further comprising changing an intensity of the stimulation based on results of the neural stimulation capture test.

13. The method of claim 1, further comprising applying rules or criteria to select valid PVCs, and applying rules or criteria to select valid R-R intervals used to detect the pre-PVC heart rate data and the post-PVC heart rate data.

14. The method of claim 1, wherein stimulating the autonomic neural target includes generating stimulation bursts, and wherein measuring HRT includes measuring HRT during a time between successive stimulation bursts when the stimulation signal is not generated.

15. The method of claim 1, wherein stimulating the autonomic neural target includes generating stimulation bursts, and wherein measuring HRT includes:
measuring HRT for a time that includes a beginning of one of the stimulation bursts to reflect heart rate from a time without neural stimulation to a time with neural stimulation; or measuring HRT includes measuring HRT for a time that includes an end of one of the stimulation bursts to reflect heart rate from a time with neural stimulation to a time without neural stimulation.

16. A neural stimulation system to modulate autonomic balance between parasympathetic tone and sympathetic tone in an autonomic nervous system (ANS), the system comprising:
a neural stimulator configured to stimulate an autonomic neural target to modulate the autonomic balance in the ANS;
a premature ventricular contraction (PVC) stimulator configured to induce a PVC using a ventricular pacing pulse;
a heart rate detector configured to detect heart both before and after the induced PVC;
an analyzer connected to the heart rate detector and configured to measure heart rate turbulence (HRT) using pre-PVC heart rate data and post-PVC heart rate data to generate an autonomic balance indicator (ABI); and
a controller configured to:
control the neural stimulator to generate a neural stimulation signal to stimulate the autonomic neural target;
receive or generate a triggering signal representing a demand for a neural stimulation threshold test;
control the PVC stimulator in response to the triggering signal to induce the PVC; and
receive the ABI from the analyzer for the induced PVC, wherein the received ABI indicates whether the neural stimulation signal evokes a response above a threshold.

17. The system of claim 16, wherein the controller is configured to automatically evaluate whether the neural stimulation signal evokes the response above the threshold, to adjust the neural stimulation signal if the neural stimulation signal did not evoke the response above the threshold, and generate another triggering signal to demand another neural stimulation threshold test for the adjusted neural stimulation signal.

18. The system of claim 16, wherein the controller is adapted to make an adjustment to the neural stimulation therapy using at least two of ABIs.

19. The system of claim 16, further comprising communication circuitry configured to communicate with a programmer configured for use by a clinician to program the neural stimulator, wherein the controller and the communication circuitry are configured to cooperate to communicate the received ABI to the programmer.

20. The system of claim 16, further comprising communication circuitry configured to communicate with a programmer, wherein the controller and communication circuitry are configured to receive the triggering signal from the programmer.

21. The system of claim 16, further comprising a timer, wherein the controller and timer are configured to generate the triggering signal based on time.

22. The system of claim 16, further comprising an event detector, wherein the controller and timer are configured to generate the triggering signal based on a detected event.

23. The system of claim 16, wherein the neural stimulator, the PVC stimulator, the heart rate detector, the analyzer, and the controller are housed in a single implantable medical device.

24. The system of claim 16, further comprising an implantable neural stimulator device and an implantable cardiac rhythm management (CRM) device adapted to communicate with each other, the implantable neural stimulator device including at least the neural stimulator and the controller, the implantable CRM device including at least the PVC stimulator.

25. The system of claim 16, wherein:
the analyzer is adapted to generate a plurality of ABIs; and
the controller is adapted to average or trend the plurality ABIs, and to control the neural stimulating using the average or trend of the plurality of ABIs to achieve the desired autonomic balance for the ANS.

26. The system of claim 16, wherein the PVC event detector is adapted to apply rules or criteria to select valid PVCs and to select valid R-R intervals used to determine pre-PVC and post-PVC heart rate data.

27. The system of claim 16, wherein the controller and the neural stimulator are configured to chronically deliver an intermittent neural stimulation therapy with stimulation bursts, and wherein the system is configured to measure HRT for a time between successive stimulation bursts when the stimulation signal is not generated.

28. The system of claim 16, wherein the controller and the neural stimulator are configured to chronically deliver an intermittent neural stimulation therapy with stimulation bursts, and wherein the system is configured to measure HRT for a time that includes a beginning of one of the stimulation bursts to reflect heart rate from a time without neural stimulation to a time with neural stimulation, or for a time that includes an end of one of the stimulation bursts to reflect heart rate from a time with neural stimulation to a time without neural stimulation.

* * * * *